(12) United States Patent
Kawano et al.

(10) Patent No.: US 6,610,694 B1
(45) Date of Patent: Aug. 26, 2003

(54) CONDENSED PYRIDAZINE COMPOUNDS, THEIR PRODUCTION AND USE

(75) Inventors: Yasuhiko Kawano, Suita (JP); Hideaki Nagaya, Toyonaka (JP); Michiyo Gyoten, Daito (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/806,652

(22) PCT Filed: Oct. 5, 1999

(86) PCT No.: PCT/JP99/05469

§ 371 (c)(1),
(2), (4) Date: Apr. 2, 2001

(87) PCT Pub. No.: WO00/20417

PCT Pub. Date: Apr. 13, 2000

(30) Foreign Application Priority Data

Oct. 6, 1998 (JP) .......................................... 10-283766
Oct. 6, 1998 (JP) .......................................... 10-283772

(51) Int. Cl.[7] ....................... A61K 31/50; A61K 31/501
(52) U.S. Cl. ................. 514/252.04; 514/183; 514/248; 544/236
(58) Field of Search ................................ 514/248, 183, 514/252.04; 544/236

(56) References Cited

U.S. PATENT DOCUMENTS

| | | | |
|---|---|---|---|
| 3,878,217 A | 4/1975 | Carr et al. ............. | 260/293.64 |
| 4,499,088 A | 2/1985 | Takaya et al. ............... | 514/202 |
| 4,908,365 A | 3/1990 | Buzas et al. ................ | 514/252 |
| 5,145,850 A | 9/1992 | Miyake et al. ............... | 514/248 |
| 5,155,108 A | 10/1992 | Miyake et al. ............... | 514/248 |
| 5,202,324 A | 4/1993 | Miyake et al. ............... | 514/248 |
| 5,369,104 A | 11/1994 | Miyake et al. ............... | 514/212 |
| 5,389,633 A | 2/1995 | Miyake et al. ............ | 514/233.2 |
| 5,491,145 A | 2/1996 | Miyake et al. ............... | 514/248 |
| 5,492,909 A | 2/1996 | Miyake et al. ............ | 514/233.2 |
| 5,922,712 A | 7/1999 | Miyake et al. ............... | 514/248 |
| 6,255,305 B1 * | 7/2001 | Broughton et al. ...... | 514/228.5 |

FOREIGN PATENT DOCUMENTS

| | | |
|---|---|---|
| EP | 0128536 A1 | 12/1984 |
| EP | 0381132 | 8/1990 |
| EP | 0440119 | 8/1991 |
| EP | 0444549 | 9/1991 |
| EP | 0548923 | 6/1993 |
| EP | 0562439 | 9/1993 |
| EP | 0562440 | 9/1993 |
| EP | 0620224 | 10/1994 |
| EP | 0632040 | 1/1995 |
| EP | 0648491 | 4/1995 |
| JP | 64-13090 | 1/1989 |
| WO | WO 96/08496 | 3/1996 |
| WO | WO 96/23798 | 8/1996 |
| WO | WO 98/49167 | 11/1998 |
| WO | WO 99/14203 | 3/1999 |

OTHER PUBLICATIONS

M. Abou–Gharbia et al. "New Antihistamines: Substituted Piperazine and Piperidine Derivatives as Novel H[1]–Antagonists", Journal of Medicinal Chemistry vol. 38 (1995), No. 20, pp. 4026–4032.

* cited by examiner

*Primary Examiner*—Richard L. Raymond
*Assistant Examiner*—Tamthom N. Truong
(74) *Attorney, Agent, or Firm*—Mark Chao; Elaine M. Ramesh

(57) ABSTRACT

A condensed pyridazine derivative which exhibits anti-allergic activity, anti-histaminic activity and/or eosinophil chemotaxis-inhibiting activity, anti-inflammatory activity, anti-PAF (platelet-activating factor) activity, and the like, and is useful as an agent for preventing or treating asthma, allergic conjunctivitis, allergic rhinitis, urticaria, atopic dermatitis, and the like.

28 Claims, No Drawings

CONDENSED PYRIDAZINE COMPOUNDS, THEIR PRODUCTION AND USE

This application is the National Stage of International Application No. PCT/JP99/05469, filed on Oct. 5, 1999.

TECHNICAL FIELD

The present invention relates to novel condensed pyridazine derivatives exhibiting an excellent anti-allergic, anti-histaminic, anti-inflammatory or eosinophil chemotaxis-inhibiting activity, or other activities, and useful as agents for preventing or treating atopic dermatitis, allergic rhinitis, bronchial asthma, allergic conjunctivitis, chronic urticaria, etc., their pro-drugs, methods of their production, and their use in medicaments.

BACKGROUND ART

A large number of compounds with a condensed pyridazine skeleton are currently synthesized as drugs for a variety of diseases. For example, U.S. Pat. No. 3,915,968 discloses a compound represented by the formula:

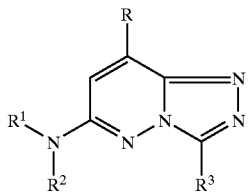

wherein R and $R^3$ independently represent a hydrogen atom or a lower alkyl group (at least one of R and $R^3$ is a lower alkyl group); $R^1$ and $R^2$ represent a heterocyclic group selected from the group consisting of pyrrolidine, piperidine, piperazine and morpholine taken together with the adjacent nitrogen atom; or a salt thereof. U.S. Pat. No. 4,136,182 discloses that a compound represented by the formula:

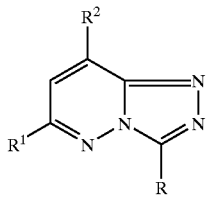

wherein R represents a hydrogen atom, a phenyl group or a lower alkylcarbonylamino group; $R^1$ represents morpholino or piperidino; $R^2$ represents a hydrogen atom or a lower alkyl group (at least one of R and $R^2$ is a group other than a hydrogen atom; when R is a phenyl group, $R^1$ is morpholino and $R^2$ is a lower alkyl group); or a salt thereof, is useful as a bronchodilator for mitigating bronchial spasms.

Also, Japanese Patent Unexamined Publication No. 279447/1994 discloses that a compound represented by the formula:

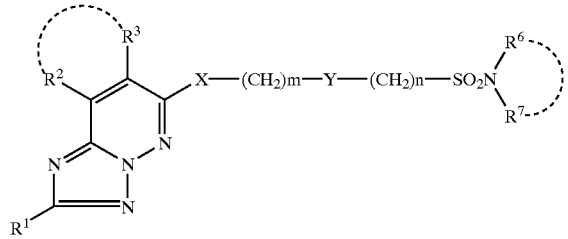

wherein $R^1$ represents a hydrogen atom, a lower alkyl group that may be substituted, or a halogen atom; $R^2$ and $R^3$ independently represent a hydrogen atom or a lower alkyl optionally having a substituent, or may form a 5- to 7-membered ring with the adjacent —C=C—; X represents an oxygen atom or S(O)p (p represents an integer from 0 to 2); Y represents a group represented by the formula:

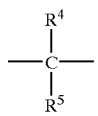

($R^4$ and $R^5$ independently represent a hydrogen atom or a lower alkyl group optionally having a substituent) or a divalent group derived from a 3- to 7-membered homocycle or heterocycle optionally having a substituent; $R^6$ and $R^7$ independently represent a hydrogen atom, a lower alkyl group optionally having a substituent, a cycloalkyl group optionally having a substituent, or an aryl group that may be substituted, or may form a nitrogen-containing heterocyclic group optionally having a substituent, with the adjacent nitrogen atom; m represents an integer from 0 to 4, and n represents an integer from 0 to 4; or a salt thereof; and, as an example synthetic product, a compound of the formula:

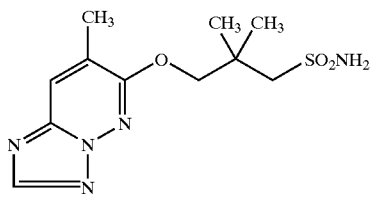

exhibits anti-asthmatic, anti-PAF, anti-inflammatory and anti-allergic activities.

Furthermore, Japanese Patent Unexamined Publication No. 279446/1994 describes a compound represented by the formula:

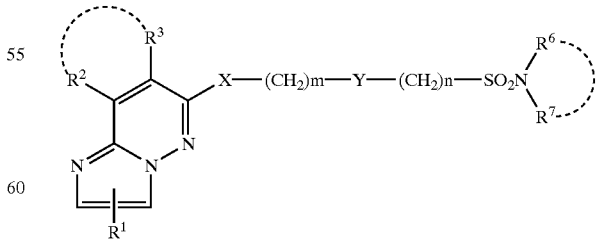

wherein $R^1$ represents a hydrogen atom, a lower alkyl group optionally having a substituent, or a halogen atom; $R^2$ and $R^3$ independently represent a hydrogen atom or a lower alkyl group optionally having a substituent (provided that either of $R^2$ and $R^3$ is a hydrogen atom, the other represents a lower alkyl group optionally having a substituent), or may form a 5- to 7-membered ring taken together with the adjacent —C=C—; X represents an oxygen atom or S(O)p (p represents an integer from 0 to 2); Y represents a group represented by the formula:

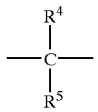

($R^4$ and $R^5$ independently represent a hydrogen atom or a lower alkyl group optionally having a substituent) or a divalent group derived from a 3- to 7-membered homocycle or heterocycle optionally having a substituent; $R^6$ and $R^7$ independently represent a hydrogen atom, a lower alkyl group optionally having a substituent, a cycloalkyl group optionally having a substituent, or an aryl group optionally having a substituent, or may form a nitrogen-containing heterocyclic group optionally having a substituent, taken together with the adjacent nitrogen atom; m represents an integer from 0 to 4, and n represents an integer from 0 to 4; or a salt thereof; and discloses that these compounds possess anti-allergic, anti-inflammatory and anti-PAF (platelet activating factor) activities to suppress bronchial spasms and bronchial contraction, and can be used as effective anti-asthmatic agents.

On the other hand, as compounds possessing anti-allergic or anti-histaminic activities, there may be mentioned, for example, terfenadine (The Merck Index, 12th edition, 9307) and ebastine (The Merck Index, 12th edition, 3534), which are already in clinical use.

In addition, EP128536 discloses anti-bacterial compounds represented by the formula:

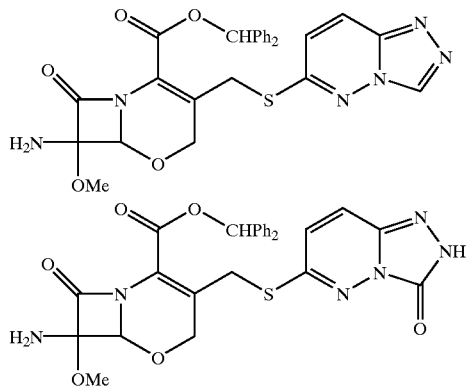

and so on, and U.S. Pat. No. 4,499,088 discloses antibacterial compounds represented by the formula:

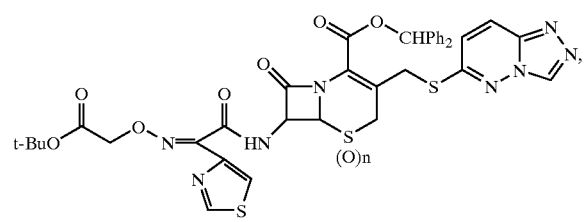

and so on. However, no description is given about anti-allergic activity, anti-histaminic activity, anti-inflammatory activity and so on.

There is demand for the development of novel compounds more satisfactory than conventional anti-allergic agents, anti-histaminic agents, anti-inflammatory agents etc. in terms of activity efficacy, sustained activity, safety etc.

DISCLOSURE OF THE INVENTION

After various extensive investigations to resolve the above problems, the present inventors synthesized for the first time (1) a novel condensed pyridazine compound, owing to its unique chemical structure characterized by the presence of substituted piperidine or piperazine via a spacer from the 6-position of the triazolo[4,3-b]pyridazine skeleton, or a salt thereof, and (2) a novel condensed pyridazine compound, owing to its unique chemical structure characterized by the presence of substituted piperidine or piperazine via a spacer from the 6-position of the [1,2,4]triazolone[4,3-b]pyridazine skeleton, or a salt thereof, and found that these compounds exhibit unexpectedly excellent anti-allergic, anti-histaminic, anti-inflammatory, eosinophil chemotaxis-inhibiting activity, and excellent sustained activity and safety, based on their unique chemical structures, and are useful as preventive or therapeutic agents for atopic dermatitis, allergic rhinitis, bronchial asthma, allergic conjunctivitis, chronic urticaria, etc., based on these pharmacological activities. The inventors conducted further investigations based on these findings, and developed the present invention.

The present invention provides:

(1) A compound represented by the formula:

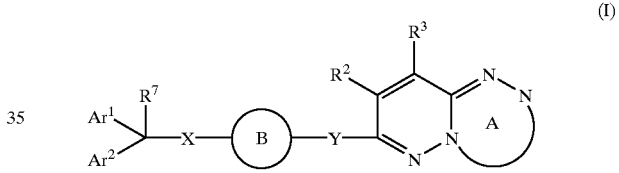

wherein Ring A is a ring represented by the formula:

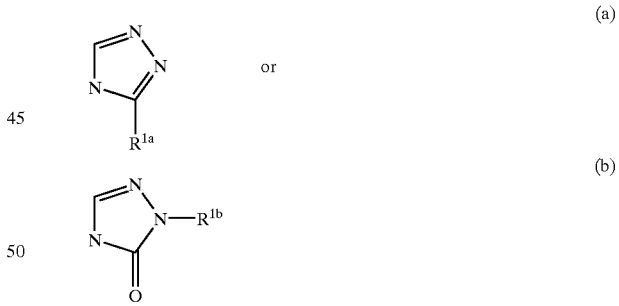

(wherein $R^{1a}$ is a hydrogen atom, a halogen atom, a hydrocarbon group optionally having a substituent, an acyl group or a hydroxy group having a substituent; $R^{1b}$ is a hydrogen atom, a halogen atom, a hydrocarbon group optionally having a substituent, an acyl group or a hydroxy group optionally having a substituent); $Ar^1$ and $Ar^2$ are independently an aromatic group optionally having a substituent, and may form a condensed ring group with an adjacent carbon atom; Ring B is a nitrogen-containing heterocycle optionally having a substituent; X and Y, whether identical or not, are a bond, an oxygen atom, S(O)p (p is an integer from 0 to 2), $NR^4$ wherein $R^4$ is a hydrogen atom or a lower alkyl group, or a divalent linear lower hydrocarbon group which may have a substituent, and which may contain 1 to 3 hetero atoms; $R^2$ and $R^3$, whether identical or not, are a hydrogen atom, a halogen atom, a hydrocarbon group optionally having a substituent, an acyl group or a hydroxy group optionally having a substituent; $R^7$ is a hydrogen atom, a hydroxy group which may be substituted by lower alkyl or a carboxyl group; provided that Ring B is not a heterocycle represented by the formula:

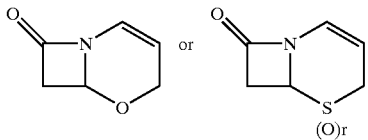

wherein r is 0 or 1, or a salt thereof,
(2) A compound as defined in term (1) wherein $Ar^1$ and $Ar^2$ are independently an aromatic hydrocarbon group optionally having a substituent,
(3) A compound as defined in term (1) wherein $Ar^1$ and $Ar^2$ are independently a phenyl group optionally having a substituent,
(4) A compound as defined in term (1) wherein $Ar^1$ and $Ar^2$ are independently
  (1) a phenyl group which may be substituted by a halogen atom or $C_{1-6}$ alkyl, or
  (2) a 5- to 8-membered aromatic heterocyclic group containing 1 to 4 hetero atoms selected from among a nitrogen atom, a sulfur atom and an oxygen atom, in addition to carbon atoms,
(5) A compound as defined in term (1) wherein Ring B is a ring represented by the formula:

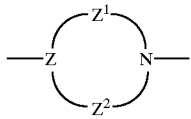

wherein Z is a nitrogen atom or a methine group, $Z^1$ and $Z^2$ are independently a linear $C_{1-4}$ alkylene group which may be substituted by a hydroxy group, an oxo group or a $C_{1-6}$ alkyl group,
(6) A compound as defined in term (1) wherein X is a bond, an oxygen atom or NH,
(7) A compound as defined in term (1) wherein Y is
  (i) a $C_{1-6}$ alkylene group,
  or a group represented by the formula:
    (ii) —$(CH_2)p^1O$—,
    (iii) —$(CH_2)p^1NH$—,
    (iv) —$(CH_2)p^1S$—,
    (v) —$(CH_2)q^1CH(OH)(CH_2)q^2O$—,
    (vi) —$(CH_2)q^1CH(OH)(CH_2)q^2NH$—,
    (vii) —$(CH_2)q^1CH(OH)(CH_2)q^2S$—,
    (viii) —$(CH_2)p^1CONH$—,
    (ix) —$COO(CH_2)p^1O$—,
    (x) —$COO(CH_2)p^1NH$—,
    (xi) —$COO(CH_2)p^1S$—,
    (xii) —$(CH_2)q^1O(CH_2)q^2O$—,
    (xiii) —$(CH_2)q^1O(CH_2)q^2NH$— or
    (xiv) —$(CH_2)q^1O(CH_2)q^2S$— wherein $p^1$ is an integer from 1 to 6, $q^1$ and $q^2$ are independently an integer from 1 to 3,
(8) A compound as defined in term (1) wherein Y is a group represented by the formula:

—$(CH_2)m\text{-}Y^1\text{—}(CH_2)n\text{-}Y^2$— wherein $Y^1$ and $Y^2$ are independently a bond, an oxygen atom, S(O)p (p is an integer from 0 to 2), $NR^4$ ($R^4$ is a hydrogen atom or a lower alkyl group), a carbonyl group, a carbonyloxy group or a group represented by the formula:

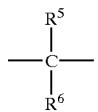

wherein $R^5$ and $R^6$, whether identical or not, are a hydroxy group or a $C_{1-4}$ alkyl group; m and n are independently an integer from 0 to 4 (sum of m and n is not more than 6),
(9) A compound as defined in term (1) wherein $R^{1a}$ is
  (1) a hydrogen atom,
  (2) a carboxyl group,
  (3) a $C_{1-6}$ alkoxy-carbonyl group,
  (4) a $C_{1-6}$ alkyl group which may be substituted by a group selected from the group consisting of (i) cyano, (ii) carboxyl, (iii) $C_{1-6}$ alkoxy-carbonyl and (iv) carbamoyl, or
  (5) a carbamoyl group which may be substituted by a $C_{1-6}$ alkyl group optionally having carboxyl or $C_{1-6}$ alkoxy-carbonyl,
(10) A compound as defined in term (1) wherein $R^{1b}$ is
  (1) a hydrogen atom, or
  (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl,
(11) A compound as defined in term (1) wherein $R^2$ and $R^3$ are a hydrogen atom,
(12) A compound as defined in term (1) wherein $R^7$ is a hydrogen atom or a hydroxy group,
(13) A compound as defined in term (1) wherein $Ar^1$ and $Ar^2$ are independently a phenyl group which may be substituted; Ring B is a ring represented by the formula:

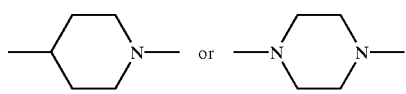

X is a bond or an oxygen atom;
Y is a group represented by the formula:

—$(CH_2)m\text{-}Y^3\text{—}(CH_2)n\text{-}Y^4$— wherein $Y^3$ is a bond or —CH(OH)—, $Y^4$ is an oxygen atom, S or NH, and m and n are independently an integer from 0 to 6 (sum of m and n is not more than 6);
$R^{1a}$ is
  (1) a hydrogen atom,
  (2) a carboxyl group,
  (3) a $C_{1-6}$ alkoxy-carbonyl group,
  (4) a $C_{1-6}$ alkyl group which may be substituted by a group selected from the group consisting of (i) cyano, (ii) carboxyl, (iii) $C_{1-6}$ alkoxy-carbonyl and (iv) carbamoyl, or
  (5) a carbamoyl group which may be substituted by a $C_{1-6}$ alkyl group optionally having carboxyl or $C_{1-6}$ alkoxy-carbonyl;

$R^{1b}$ is
- (1) a hydrogen atom, or
- (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl;

$R^2$, $R^3$ and $R^7$ are a hydrogen atom,

(14) A compound represented by the formula:

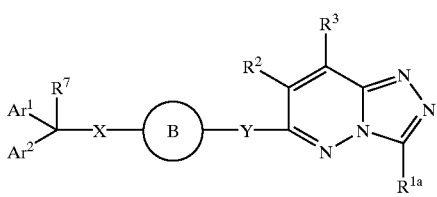

(Ia)

wherein the symbols have the same definitions as those shown in term (1), or a salt thereof,

(15) A compound as defined in term (14) wherein $Ar^1$ and $Ar^2$ are independently a phenyl group which may be substituted; Ring B is a ring represented by the formula:

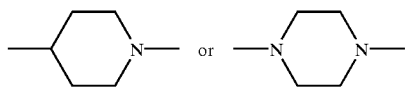

X is a bond or an oxygen atom; Y is a group represented by the formula:

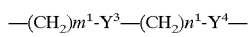

—(CH$_2$)$m^1$-Y$^3$—(CH$_2$)$n^1$-Y$^4$— wherein $Y^3$ is a bond or —CH(OH)—, $Y^4$ is an oxygen atom, S or NH, and $m^1$ and $n^1$ are independently an integer from 0 to 4 (sum of $m^1$ and $n^1$ is not more than 6); $R^{1a}$ is (1) a hydrogen atom, (2) a carboxyl group, (3) a $C_{1-6}$ alkoxy-carbonyl group, (4) a $C_{1-6}$ alkyl group which may be substituted by a group selected from the group consisting of (i) cyano, (ii) carboxyl, (iii) $C_{1-6}$ alkoxy-carbonyl and (iv) carbamoyl, or (5) a carbamoyl group which may be substituted by a $C_{1-6}$ alkyl group optionally having carboxyl or $C_{1-6}$ alkoxy-carbonyl; and $R^2$, $R^3$ and $R^7$ are a hydrogen atom,

(16) ① 6-[6-[4-(diphenylmethoxy)piperidino]hexyloxy][1,2,4]triazolo[4,3-b]pyridazine, ② 6-[6-[4-(diphenylmethoxy)piperidino]hexylamino][1,2,4]triazolo[4,3-b]pyridazine, ③ 3-tert-butyl-6-[3-[4-(diphenylmethoxy)piperidino]propoxy][1,2,4]triazolo[4,3-b]pyridazine, ④ 6-[3-[4-(diphenylmethoxy)piperidino]propylamino][1,2,4]triazolo[4,3-b]pyridazine-3-carboxylic acid, or a salt thereof,

(17) A compound represented by the formula:

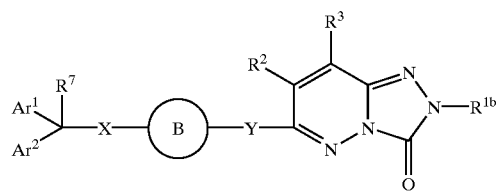

(Ib)

wherein the symbols have the same meanings as defined in term (1), or a salt thereof,

(18) A compound as defined in term (17) wherein the partial structural formula:

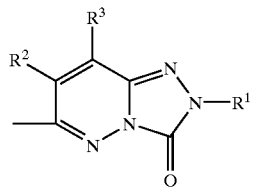

(wherein the symbols have the same meanings as defined in term (1)) represents the formula:

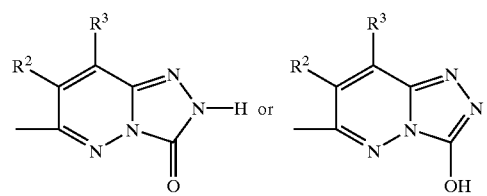

(wherein the symbols have the same meanings as defined in term (1)), provided that $R^{1b}$ is a hydrogen atom,

(19) A compound as defined in term (17) wherein $Ar^1$ and $Ar^2$ are independently a phenyl group which may be substituted; Ring B is a ring represented by the formula:

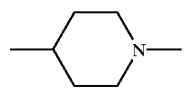

X is an oxygen atom; Y is a group represented by the formula:

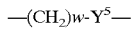

—(CH$_2$)$w$-Y$^5$— wherein w is an integer from 1 to 6, and $Y^5$ is an oxygen atom or NH; $R^{1b}$ is
- (1) a hydrogen atom, or
- (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl; and $R^2$, $R^3$ and $R^7$ are a hydrogen atom,

(20) ① 6-[3-[4-(diphenylmethoxy)piperidino]propylamino][1,2,4]triazolo[4,3-b]pyridazin-3(2H)-one, ② ethyl 2-[6-[3-[4-(diphenylmethoxy)piperidino]propylamino]-3-oxo[1,2,4]triazolo[4,3-b]pyridazin-2(3H)-yl]-2-methylpropionate, ③ 2-[6-[3-[4-(diphenylmethoxy)piperidino]propylamino]-3-oxo[1,2,4]triazolo[4,3-b]pyridazin-2(3H)-yl]-2-methylpropionic acid,
④ 4pivaloyloxymethyl 2-[6-[3-[4-(diphenylmethoxy)piperidino]propylamino]-3-oxo[1,2,4]triazolo[4,3-b]pyridazin-2(3H)-yl]-2-methylpropionate,
⑤ pivaloyloxymethyl 2-[6-[3-[4-(diphenylmethoxy)piperidino]propoxy]-3-oxo[1,2,4]triazolo[4,3-b]pyridazin-2(3H)-yl]-2-methylpropionate, or a salt thereof,

(21) A pro-drug of a compound as defined in term (1).

(22) A method for producing a compound as defined in term (1), which comprises reacting a compound represented by the formula:

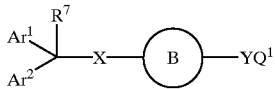

wherein $Q^1$ represents a leaving group; the other symbols have the same meanings as defined in term (1), or a salt thereof, with a compound represented by the formula:

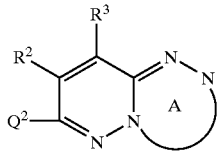

wherein $Q^2$ represents a leaving group; the other symbols have the same meanings as defined in term (1), or a salt thereof,

(23) A method for producing a compound as defined in term (14), which comprises reacting a compound represented by the formula:

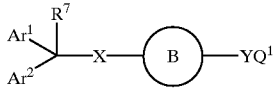

wherein $Q^1$ represents a leaving group; the other symbols have the same meanings as defined in term (1), or a salt thereof, with a compound represented by the formula:

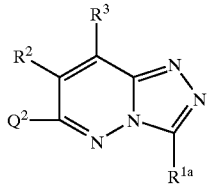

wherein $Q^2$ represents a leaving group; the other symbols have the same meanings as defined in term (1), or a salt thereof,

(24) A method for producing a compound as defined in term (17), which comprises reacting a compound represented by the formula:

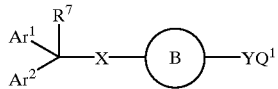

wherein $Q^1$ represents a leaving group; the other symbols have the same meanings as-defined in term (1), or a salt thereof, with a compound represented by the formula:

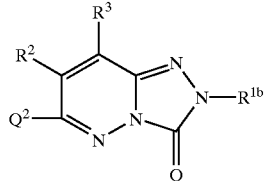

wherein $Q^2$ represents a leaving group; the other symbols have the same meanings as defined in term (1), or a salt thereof,

(25) A pharmaceutical composition containing a compound as defined in term (1) or a pro-drug as defined in term (21),

(26) A pharmaceutical composition as defined in term (25) which is an anti-histaminic and/or eosinophil chemotaxis-inhibiting agent,

(27) A pharmaceutical composition as defined in term (25) which is an anti-allergic agent,

(28) A pharmaceutical composition as defined in term (25) which is an agent for preventing or treating asthma, allergic conjunctivitis, allergic rhinitis, chronic urticaria or atopic dermatitis,

(29) A method for suppressing histamine and/or eosinophil chemotaxis comprising administering an effective amount of a compound as defined in term (1) or a pro-drug as defined in term (21) to mammals,

(30) A method for treating allergic diseases comprising administering an effective amount of a compound as defined in term (1) or a pro-drug as defined in term (21) to mammals,

(31) A method for treating asthma, allergic conjunctivitis, allergic rhinitis, chronic urticaria or atopic dermatitis which comprises administering an effective amount of a compound as defined in term (1) or a pro-drug as defined in term (21) to mammals,

(32) Use of a compound as defined in term (1) or a pro-drug as defined in term (21) for producing an anti-histaminic and/or eosinophil chemotaxis-inhibiting agent,

(33) Use of a compound as defined in term (1) or a pro-drug as defined in term (21) for producing an anti-allergic agent, and

(34) Use of a compound as defined in term (1) or a pro-drug as defined in term (21) for producing an agent for preventing or treating asthma, allergic conjunctivitis, allergic rhinitis, chronic urticaria or atopic dermatitis.

And, the present invention also provides:

(35) A compound as defined in term (1) wherein $Ar^1$ and $Ar^2$ are independently ① a $C_{6-14}$ aromatic hydrocarbon group, or ② a 5- to 8-membered aromatic heterocyclic group containing 1 to 4 hetero atoms selected from a nitrogen atom, a sulfur atom and an oxygen atom, in addition to carbon atoms, or ③ a monovalent group resulting from removal of an optionally selected hydrogen atom from a condensed ring formed by said aromatic heterocyclic group and $C_{6-14}$ aromatic hydrocarbon group, which $C_{6-14}$ aromatic hydrocarbon group, 5- to 8-membered aromatic heterocyclic group and monovalent group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo; and $Ar^1$ and $Ar^2$, along with the adjacent carbon atom, may form a condensed cyclic group represented by the formula:

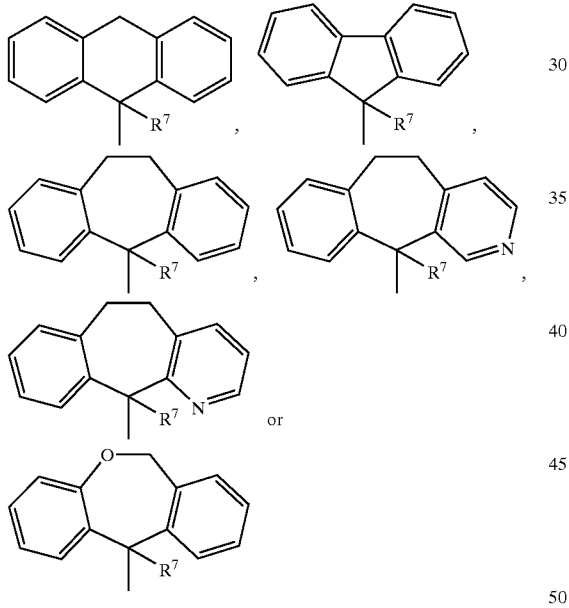

wherein $R^7$ is a hydrogen atom, a hydroxy group which may be substituted by $C_{1-6}$ alkyl or a carboxyl group, which condensed cyclic group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkylcarbonyl, (xvii) carboxyl, (xviii) $C_{1-6}$ alkoxy-carbonyl, (xix) carbamoyl (or carbamoyl), (xx) mono-$C_{1-6}$ alkyl-carbamoyl (or mono-$C_{1-6}$ alkyl-carbamoyl), (xxi) di-$C_{1-6}$ alkyl-carbamoyl (or di-$C_{1-6}$ alkyl-carbamoyl), (xxii) $C_{6-10}$ aryl-carbamoyl (or $C_{6-10}$ aryl-carbamoyl), (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo; the ring B is a 3- to 13-membered nitrogen-containing heterocycle which contains at least one nitrogen atom, and which may contain 1 to 3 hetero atoms selected from among a nitrogen atom, an oxygen atom and a sulfur atom, which 3- to 13-membered nitrogen-containing heterocycle may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo; X and Y, whether identical or not, are ① a bond, ② an oxygen atom, ③ S(O)p wherein p is an integer from 0 to 2, ④ $NR^4$ wherein $R^4$ is a hydrogen atom or a linear or branched $C_{1-6}$ alkyl group or ⑤ a divalent linear $C_{1-6}$ hydrocarbon group which may contain 1 to 3 hetero atoms selected from among an oxygen atom and a sulfur atom, and which optionally have a substituent selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo; $R^{1a}$ is (1) a hydrogen atom,
(2) a halogen atom,
(3) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy groups, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) C16 alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo; (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo, (4) an acyl group represented by the formula —(C=O)—$R^8$, —$SO_2$—$R^8$, —SO—$R^8$, —(C=O)$NR^8R^9$, —(C=O)O—$R^8$, —(C=S)O—$R^8$ or —(C=S)$NR^8R^9$ wherein $R^8$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy groups, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ ararkyloxy and (xxviii) oxo, or (c) a group represented by the formula —$OR^{10}$ wherein $R^{10}$ is a hydrogen atom or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy groups, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_6$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo, $R^6$ is a hydrogen atom or a $C_{1-6}$ alkyl group, or (5) a group represented by the formula —$OR^1$ wherein $R^1$ is a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy groups, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, c(xxvi) $C_{6-10}$ aryloxy, (xxvii) $C_{7-16}$ aralkyloxy and (xxviii) oxo;

$R^{1b}$, $R^2$ and $R^3$ are independently (1) a hydrogen atom, (2) a halogen atom, (3) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1-to 3 $C_{1-6}$ alkoky groups, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo, (4) an acyl group represented by the formula —(C=O)—$R^{12}$, —$SO_2$—$R^{12}$, —SO—$R^{12}$, —(C=O)$NR^{12}R^{13}$, —(C=O)O—$R^{12}$, —(C=S)O—$R^{12}$ or —(C=S)$NR^{12}R^{13}$ wherein $R^{12}$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy groups, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo, or (c) a group represented by the formula —$OR^{14}$ wherein $R^{14}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo, $R^{13}$ is a hydrogen atom or a $C_{1-6}$ alkyl group; or (5) a group represented by the formula —$OR^{15}$ wherein $R^{15}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 $C_{1-6}$ alkoxy, a $C_{6-14}$ aryl group or a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 halogen atoms, mono- or di-$C_{1-6}$ alkylamino or $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5- or 6-membered cyclic amino, (xvi) $C_{1-6}$ alkyl-carbonyl, (xvii) carboxyl, (xviii) $C_{1-6}$ alkoxy-carbonyl, (xix) carbamoyl or thiocarbamoyl, (xx) mono-$C_{1-6}$ alkyl-carbamoyl or mono-$C_{1-6}$ alkyl-thiocarbamoyl, (xxi) di-$C_{1-6}$ alkyl-carbamoyl or di-$C_{1-6}$ alkyl-thiocarbamoyl, (xxii) $C_{6-10}$ aryl-carbamoyl or $C_{6-10}$ aryl-thiocarbamoyl, (xxiii) sulfo, (xxiv) $C_{1-6}$ alkylsulfonyl, (xxv) $C_{6-10}$ aryl, (xxvi) $C_{6-10}$ aryloxy, (xxvii) $C_{7-16}$ aralkyloxy and (xxviii) oxo;

$R^7$ is a hydrogen atom, a hydroxy group which may be substituted by $C_{1-6}$ alkyl, or a carboxyl group.

Furthermore, when Compound (I) or a salt thereof has asymmetric carbon atoms in the structure thereof, optical isomers and racemates are included in the scope of the present invention. Compound (I) or a salt thereof may be a hydrate or anhydrate.

BEST MODES OF EMBODIMENT OF THE INVENTION

In Formula (I) above, ring A is a ring represented by the formula:

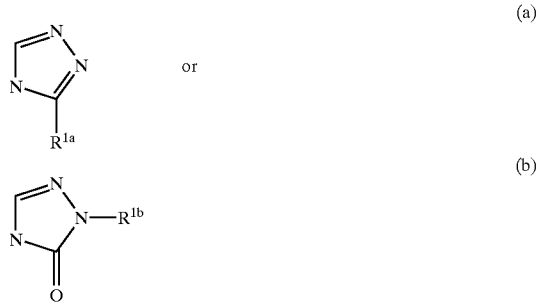

wherein $R^{1a}$ is a hydrogen atom, a halogen atom, a hydrocarbon group optionally having a substituent, an acyl group or a hydroxy group having a substituent; $R^{1b}$ is a hydrogen atom, a halogen atom, a hydrocarbon group optionally having a substituent, an acyl group or a hydroxy group having a substituent.

With respect to Formula (I) above, Compound (I) wherein Ring A is Type (a) and Compound (I) wherein Ring A is Type (b) are hereinafter referred to as Compound (Ia) and Compound (Ib), respectively.

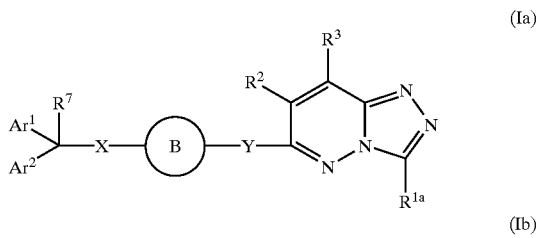

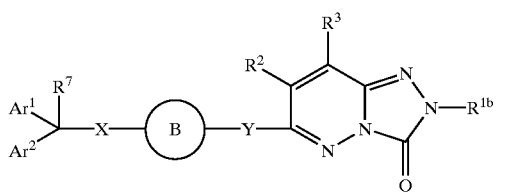

In Formula (I) above, $Ar^1$ and $Ar^2$ are an "aromatic group optionally having a substituent," and may form a condensed ring group with an adjacent carbon atom.

Examples of the "aromatic group" represented by $Ar^1$ and $Ar^2$ include ① monocyclic or condensed polycyclic aromatic hydrocarbon groups, specifically 6- to 14-membered monocylic or condensed polycyclic aromatic hydrocarbon groups such as $C_{6-14}$ aryl groups (e.g., phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl, 9-phenanthryl, etc.) (preferably phenyl, tolyl, xylyl, biphenyl, 1-naphthyl, 2-naphthyl, etc., particularly preferably phenyl, etc.), or ② monocyclic groups (preferably 5- to 8-membered) containing 1 or more (e.g., 1 to 4, preferably 1 to 3) of one or two kinds of hetero atoms selected from among a nitrogen atom, a sulfur atom and an oxygen atom, in addition to carbon atoms, or condensed aromatic heterocyclic groups thereof, specifically aromatic heterocycles such as thiophene, benzo[b]thiophene, benzo[b]furan, benzimidazole, benzoxazole, benzothiazole, benzisothiazole, naphtho[2,3-b]thiophene, thianthrene, furan, indolizine, xanthrene, phenoxathin, pyrrole, imidazole, triazole, thiazole, oxazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, isothiazole, phenothiazine, isoxazole, furazan, phenoxazine and isochroman (preferably pyridine, thiophene, furan, etc., more preferably pyridine etc.), or monovalent groups resulting from removal of an optionally selected hydrogen atom from a condensed ring formed by one of these rings (preferably monocyclic heterocycles mentioned above) and one or more than one (preferably 1 or 2, more preferably 1) aromatic ring (e.g., aromatic hydrocarbon groups mentioned above, preferably benzene ring, etc.).

The "aromatic group" of the "aromatic group optionally having a substituent" represented by $Ar^1$ and $Ar^2$ is preferably phenyl or the like.

Examples of the "substituent" for the aromatic group represented by $Ar^1$ and $Ar^2$ include: (i) halogen atoms (e.g., fluorine, chlorine, bromine, iodine), (ii) lower alkylenedioxy groups (e.g., $C_{1-3}$ alkylenedioxy groups such as methylenedioxy and ethylenedioxy), (iii) nitro groups, (iv) cyano groups, (v) optionally halogenated lower alkyl groups, (vi) optionally halogenated lower alkenyl groups, (vii) optionally halogenated lower alkynyl groups, (viii) lower cycloalkyl groups (e.g., $C_{3-6}$ cycloalkyl groups such as cyclopropyl, cyclobutyl, cyclopentyl and cyclohexyl), (ix) lower alkoxy groups which may be substituted, (x) optionally halogenated lower alkylthio groups, (xi) hydroxy groups, (xii) amino groups, (xiii) mono-lower alkylamino groups (e.g., mono-$C_{1-6}$ alkylamino groups such as methylamino, ethylamino, propylamino, isopropylamino and butylamino), (xiv) di-lower alkylamino groups (e.g., di-$C_{1-6}$ alkylamino groups such as dimethylamino, diethylamino, dipropylamino and dibutylamino), (xv) 5- or 6-membered cyclic amino groups (e.g., morpholino, piperazin-1-yl, piperidino, pyrrolidin-1-yl), (xvi) lower alkyl-carbonyl groups (e.g., $C_{1-6}$ alkylcarbonyl groups such as acetyl and propionyl), (xvii) carboxyl groups, (xviii) lower alkoxy-carbonyl groups (e.g., $C_{1-6}$ alkoxy-carbonyl groups such as methoxycarbonyl, ethoxycarbonyl, propoxycarbonyl and butoxycarbonyl), (xix) carbamoyl groups or thiocarbamoyl groups, (xx) mono-lower alkyl-carbamoyl groups (e.g., mono-$C_{1-6}$ alkyl-carbamoyl groups such as methylcarbamoyl and ethylcarbamoyl) or mono-lower alkyl-thiocarbamoyl groups (e.g., mono-$C_{1-6}$ alkyl-thiocarbamoyl groups such as methylthiocarbamoyl and ethylthiocarbamoyl), (xxi) di-lower alkyl-carbamoyl groups (e.g., di-$C_{1-6}$ alkylcarbamoyl groups such as dimethylcarbamoyl and diethylcarbamoyl) or di-lower alkyl-thiocarbamoyl groups (e.g., di-$C_{1-6}$ alkylthiocarbamoyl groups such as dimethylthiocarbamoyl and diethylthiocarbamoyl), (xxii) aryl-carbamoyl (e.g., $C_{6-10}$ aryl-carbamoyl such as phenylcarbamoyl and naphthylcarbamoyl) or aryl-thiocarbamoyl (e.g., $C_{6-10}$ aryl-thiocarbamoyl such as phenylthiocarbamoyl and naphthylthiocarbamoyl), (xxiii) sulfo groups, (xxiv) lower alkylsulfonyl groups (e.g., $C_{1-6}$ alkylsulfonyl groups such as methylsulfonyl and ethylsulfonyl), (xxv) aryl groups (e.g., $C_{6-10}$ aryl groups such as phenyl and naphthyl), (xxvi) aryloxy groups (e.g., $C_{6-10}$ aryloxy groups such as phenyloxy and naphthyloxy), (xxvii) aralkyloxy groups (e.g., $C_{7-16}$ aralkyloxy groups such as benzyloxy), and (xxviii) oxo groups.

Examples of the "optionally halogenated lower alkyl group" include lower alkyl groups (e.g., $C_{1-6}$ alkyl groups such as methyl, ethyl, propyl, isopropyl, butyl, isobutyl, sec-butyl, tert-butyl, pentyl and hexyl) optionally having 1 to 3 halogen atoms (e.g., fluorine, chlorine, bromine, iodine), specifically methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

Examples of the "optionally halogenated lower alkenyl group" and "optionally halogenated lower alkynyl group" include lower alkenyl groups (e.g., $C_{2-6}$ alkenyl groups such as vinyl, propenyl, isopropenyl, 2-buten-1-yl, 4-penten-1-yl and 5-hexen-1-yl) optionally having 1 to 3 halogen atoms (e.g., fluorine, chlorine, bromine, iodine) and lower alkynyl groups (e.g., $C_{2-6}$ alkynyl groups such as 2-butyn-1-yl, 4-pentyn-1-yl and 5-hexyn-1-yl) optionally having 1 to 3 halogen atoms (e.g., fluorine, chlorine, bromine, iodine).

Examples of the "lower alkoxy groups which may be substituted" include lower alkoxy groups (e.g., $C_{1-6}$ alkoxy groups such as methoxy, ethoxy, propoxy, isopropoxy, n-butoxy, isobutoxy, sec-butoxy and tert-butoxy) optionally having 1 to 3 halogen atoms (e.g., fluorine, chlorine, bromine, iodine), mono- or di-lower alkylamino groups (e.g., mono- or di-$C_{1-6}$ alkylamino groups such as methylamino, dimethylamino, ethylamino and dimethylamino) or lower alkoxy-carbonyl groups (e.g., $C_{1-6}$ alkoxy-carbonyl groups such as methoxycarbonyl and ethoxycarbonyl).

Examples of the "optionally halogenated lower alkylthio group" include lower alkylthio groups (e.g., $C_{1-6}$ alkylthio groups such as methylthio, ethylthio, n-propylthio, isopropylthio, n-butylthio, isobutylthio, sec-butylthio and tert-butylthio) optionally having 1 to 3 halogen atoms (e.g., fluorine, chlorine, bromine, iodine), specifically methylthio, difluoromethylthio, trifluoromethylthio, ethylthio, propylthio, isopropylthio, butylthio, 4,4,4-trifluorobutylthio, pentylthio and hexylthio.

Specific examples of the condensed ring formed by $Ar^1$ and $Ar^2$, along with the adjacent carbon atom, include condensed ring groups represented by the formula:

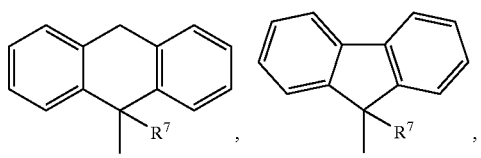

-continued

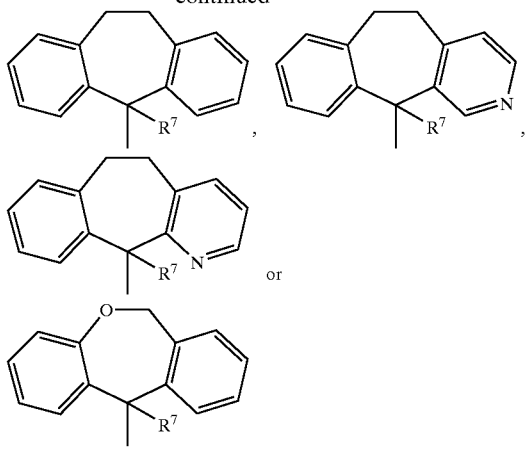

wherein R⁷ has the same definition as that shown above.

It is preferable that Ar¹ and Ar², whether identical or not, are an aromatic hydrocarbon group (e.g., $C_{6-14}$ aromatic hydrocarbon group) optionally having a substituent, and a benzene ring optionally having a substituent is more preferred. More preferably, Ar¹ and Ar² are independently (1) phenyl group which may be substituted by a halogen atom or $C_{1-6}$ alkyl, or (2) a 5- to 8-membered aromatic heterocyclic group containing 1 to 4 hetero atoms selected from among a nitrogen atom, a sulfur atom and an oxygen atom, in addition to carbon atoms.

In Formula (I) above, Ring B represents a "nitrogen-containing heterocycle optionally having a substituent," provided that Ring B is not a heterocycle represented by the formula:

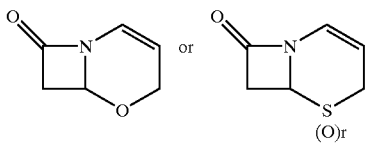

wherein r is 0 or 1.

Examples of the "nitrogen-containing heterocycle" represented by Ring B include 3- to 13-membered nitrogen-containing heterocycles which contains one nitrogen atom, which may further contain 1 to 3 hetero atoms selected from among a nitrogen atom, an oxygen atom, a sulfur atom, etc. In Formula (I) above, it is preferable that Ring B form a divalent group resulting from removal of one hydrogen atom from the nitrogen atom and other atoms of Ring B, respectively. Specific examples include 3- to 9-membered (more preferably 3- to 6-membered) nitrogen atom-containing heterocyclic groups such as

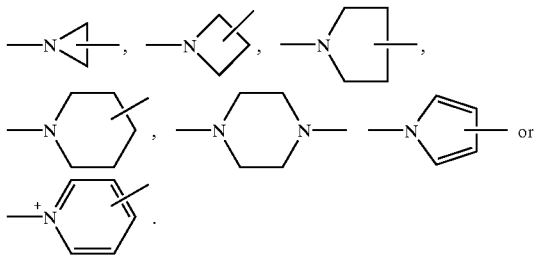

Examples of the substituent for the nitrogen-containing heterocycle represented by Ring B include the same as the substituent for the "aromatic group optionally having a substituent" represented by Ar¹ and Ar² above.

Specific preferable examples of Ring B include a ring represented by the formula:

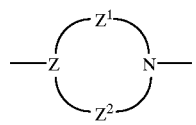

wherein Z is a nitrogen atom or a methine group, $Z^1$ and $Z^2$ are independently a linear $C_{1-4}$ alkylene group which may be substituted by a hydroxy group, an oxo group or a $C_{1-6}$ alkyl group.

Examples of said "$C_{1-6}$ alkyl group" include linear or branched $C_{1-6}$ alkyl groups such as methyl, ethyl, propyl, isopropyl, butyl, isobutyl, sec-butyl, tert-butyl, pentyl and hexyl.

Examples of said "linear $C_{1-4}$ alkylene group" include linear $C_{1-4}$ alkylene groups such as methylene, ethylene, propylene and butylene.

Preferable examples of the "linear $C_{1-4}$ alkylene group which may be substituted by a hydroxy group, an oxo group or a $C_{1-6}$ alkyl group" represented by $Z^1$ and $Z^2$ include unsubstituted linear $C_{1-4}$ alkylene groups, and unsubstituted linear $C_{1-2}$ alkylene groups are more preferred.

Ring B is more preferably piperidine, piperazine, or the like.

In Formula (I) above, X and Y, whether identical or not, are ① a bond, ② an oxygen atom, ③ S(O)p (p is an integer from 0 to 2), ④ NR⁴ wherein R⁴ is a hydrogen atom or a lower alkyl group, or ⑤ a divalent linear lower hydrocarbon group which may contain a substituent, and which may further contain 1 to 3 hetero atoms.

Examples of the lower alkyl group represented by R⁴ include linear or branched $C_{1-6}$ alkyl groups such as methyl, ethyl, propyl, isopropyl, butyl, isobutyl, sec-butyl, tert-butyl, pentyl and hexyl.

Examples of the "divalent linear lower hydrocarbon group which may further contain 1 to 3 hetero atoms" represented by X and Y include groups resulting from removal of each of hydrogen atoms (2 in total) bound to the same or different carbon atom from a lower ($C_{1-6}$) hydrocarbon, and which may optionally contain hetero atoms selected from among an oxygen atom, a sulfur atom, etc., in the hydrocarbon chain.

Specific examples of the "divalent linear lower hydrocarbon group" include (i) $C_{1-6}$ alkylene groups (e.g., —CH₂—, —(CH₂)₂—, —(CH₂)₃—, —(CH₂)₄—, —(CH₂)₅—, —(CH₂)₆—, etc.), (ii) $C_{2-6}$ alkenylene groups (e.g., —CH=CH—, —CH=CH—CH₂—, —CH₂—CH=CH—CH₂—, —(CH₂)₂—CH=CH—CH₂—, —(CH₂)₂—CH=CH—(CH₂)₂—, —(CH₂)₃—CH=CH—CH₂—, etc.), and (iii) $C_{2-6}$ alkynylene groups (e.g., —C≡C—, —C≡C—CH₂—, CH₂—C≡C—CH₂—, —(CH₂)₂—C≡C—CH₂—, —(CH₂)₂—C≡C—(CH₂)₂—, (CH₂)₃—C≡C—CH₂—, etc.).

Examples of the "substituent" for the "divalent linear lower hydrocarbon group which may further contain 1 to 3 hetero atoms," represented by X and Y include the same as the "substituent" for the "aromatic group optionally having a substituent" represented by Ar¹ and Ar² above, and is preferably a hydroxy group or an oxo group.

X is preferably a bond, an oxygen atom or NH, and a bond or an oxygen atom is particularly preferred.

Preferable examples of Y include a group represented by the formula:

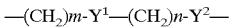

wherein $Y^1$ and $Y^2$ whether identical or not, are a bond, an oxygen atom, S(O)p wherein p has the same definition as that shown above, $NR^4$ wherein $R^4$ has the same definition as that shown above, a carbonyl group, a carbonyloxy group or a group represented by the formula:

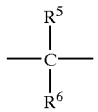

wherein $R^5$ and $R^6$, whether identical or not, are a hydroxy group or a $C_{1-4}$ alkyl group; m and n are independently an integer from 0 to 4 (sum of m and n is not more than 6).

Examples of the "$C_{1-4}$ alkyl group" represented by $R^5$ and $R^6$ include linear or branched $C_{1-4}$ alkyl groups such as methyl, ethyl, propyl, isopropyl, butyl, isobutyl, sec-butyl and tert-butyl.

Preferable examples of Y include
(i) $C_{1-6}$ alkylene groups, (ii) —(CH$_2$)p$^1$O—,
(iii) —(CH$_2$)p$^1$NH—,
(iv) —(CH$_2$)p$^1$S—,
(v) —(CH$_2$)q$^1$CH(OH)(CH$_2$)q$^2$O—,
(vi) —(CH$_2$)q$^1$CH(OH)(CH$_2$)q$^2$NH—,
(vii) —(CH$_2$)q$^1$CH(OH)(CH$_2$)q$^2$S—,
(viii) —(CH$_2$)p$^1$CONH—,
(ix) —COO(CH$_2$)p$^1$O—,
(x) —COO(CH$_2$)p$^1$NH—,
(xi) —COO(CH$_2$)p$^1$S—,
(xii) —(CH$_2$)q$^1$O(CH$_2$)q$^2$O—,
(xiii) —(CH$_2$)q$^1$O(CH$_2$)q$^2$NH— or
(xiv) —(CH$_2$)q$^1$O(CH$_2$)q$^2$S— wherein p$^1$ is an integer from 1 to 6, q$^1$ and q$^2$ are an integer from 1 to 3.

In particular, Y is preferably a bond, —(CH$_2$)$_2$—O—, —(CH$_2$)$_3$—O—, —(CH$_2$)$_4$—O—, —(CH$_2$)$_6$—O—, —(CH$_2$)$_2$—NH—, —(CH$_2$)$_3$—NH—, —(CH$_2$)$_4$—NH—, —(CH$_2$)$_3$—S—, —CH$_2$—CH(OH)—CH$_2$—O—, —(CH$_2$)$_2$—CO—NH—, —CH$_2$—CO—NH—, —CO—O—(CH$_2$)$_2$—O—, —CO—O—(CH$_2$)$_3$—O—, —(CH$_2$)$_6$—NH—, —(CH$_2$)$_6$—S—, —(CH$_2$)$_2$—O—(CH$_2$)$_2$—O—(CH$_2$)$_2$—O—(CH$_2$)$_2$—S—, or the like.

In the case of Compound (Ia), Y is preferably a group represented by the formula:

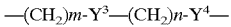

wherein $Y^3$ is a bond or —CH(OH)—, $Y^4$ is an oxygen atom, S or NH, and m and n independently are an integer from 0 to 4 (sum of m and n is not more than 6). In particular, m and n are preferably an integer from 1 to 3, and 3 is more preferred. When $Y^3$ is —CH(OH)—, m and n are preferably 1.

In the case of Compound (Ib), Y is preferably a group represented by the formula:

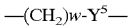

wherein w is an integer from 1 to 6, and $Y^5$ is an oxygen atom or NH. In particular, w is preferably an integer from 1 to 3, and 3 is more preferred.

In Formula (I) above, $R^{1a}$, whether identical or not, is a hydrogen atom, a halogen atom, a hydrocarbon group optionally having a substituent, an acyl group or a hydroxy group having a substituent.

$R^{1b}$, whether identical or not, is a hydrogen atom, a halogen atom, a hydrocarbon group optionally having a substituent, an acyl group or a hydroxy group having a substituent.

$R^2$ and $R^3$, whether identical or not, are a hydrogen atom, a halogen atom, a hydrocarbon group optionally having a substituent, an acyl group or a hydroxy group having a substituent.

Examples of the "halogen atom" represented by $R^{1a}$, $R^{1b}$, $R^2$ and $R^1$ include a fluorine atom, a chlorine atom, a bromine atom and an iodine atom.

Examples of the "hydrocarbon group" of the "hydrocarbon group optionally having a substituent" represented by $R^{1a}$, $R^{1b}$, $R^2$ and $R^3$ include groups resulting from removal of one hydrogen atom from a hydrocarbon compound, specifically linear or cyclic hydrocarbon groups such as alkyl groups, alkenyl groups, alkynyl groups, cycloalkyl groups, aryl groups and aralkyl groups. In particular, chain (linear or branched) or cyclic hydrocarbon groups, etc. having 1 to 16 carbon atoms are preferred, with greater preference given to (a) alkyl groups, preferably lower alkyl groups (e.g., $C_{1-6}$ alkyl groups such as methyl, ethyl, propyl, isopropyl, butyl, isobutyl, sec-butyl, tert-butyl, pentyl and hexyl), (b) alkenyl groups, preferably lower alkenyl groups (e.g., $C_{2-6}$ alkenyl groups such as vinyl, allyl, isopropenyl, butenyl, isobutenyl and sec-butenyl), (c) alkynyl groups, preferably lower alkynyl groups (e.g., $C_{2-6}$ alkynyl groups such as propargyl, ethynyl, butynyl and 1-hexynyl), (d) cycloalkyl groups, preferably lower cycloalkyl groups (e.g., $C_{3-6}$ cycloalkyl groups such as cyclopropyl, cyclobutyl, cyclopentyl, and cyclohexyl which may condense with a benzene ring optionally having 1 to 3 lower alkoxy groups (e.g., $C_{1-6}$ alkoxy groups such as methoxy), (e) aryl groups (e.g., $C_{6-14}$ aryl groups such as phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl or 9-phenanthryl, preferably phenyl groups), and (f) aralkyl groups (preferably lower aralkyl groups (e.g., $C_{7-16}$ aralkyl groups such as benzyl, phenethyl, diphenylmethyl, 1-naphthylmethyl, 2-naphthylmethyl, 2-phenylethyl, 2-diphenylethyl, 1-phenylpropyl, 2-phenylpropyl, 3-phenylpropyl, 4-phenylbutyl and 5-phenylpentyl, more preferably benzyl groups).

Examples of the "substituent" for said "hydrocarbon group" include the same as the "substituent" for the "aromatic group optionally having a substituent" represented by $Ar^1$ and $Ar^2$ above.

In particular, examples of preferred hydrocarbons include alkyl groups such as $C_{1-6}$ alkyl groups, and examples of substituents for hydrocarbon groups include cyano, carboxyl, $C_{1-6}$ alkoxy-carbonyl and carbamoyl (or thiocarbamoyl).

Examples of the "acyl group" represented by $R^{1a}$, $R^{1b}$, $R^2$ and $R^3$ include groups represented by the formula —(C=O)—$R^8$, —SO$_2$—$R^8$, —SO—$R^8$, —(C=O)NR$^8$R$^9$, —(C=O)O—$R^8$, —(C=S)O—$R^8$ or —(C=S)NR$^8$R$^9$ wherein $R^8$ is a hydrogen atom, a hydrocarbon group optionally having a substituent or a hydroxy group optionally having a substituent; and $R^9$ is a hydrogen atom or a lower alkyl group (e.g., $C_{1-6}$ alkyl group such as methyl, ethyl, propyl, isopropyl, butyl, isobutyl, sec-butyl, tert-butyl, pentyl or hexyl, preferably a $C_{1-3}$ alkyl group such as methyl, ethyl, propyl or isopropyl).

In particular, groups represented by the formula —(C=O)—$R^8$, —$SO_2$—$R^8$—, —SO—$R^8$, —(C=O)$NR^8R^9$ or —(C=O)O—$R^8$ are preferred, and groups represented by the formula —(C=O)—$R^8$ are more preferred.

The "hydrocarbon group which may be substituted" represented by $R^8$ is the same as the "hydrocarbon group optionally having a substituent" represented by $R^{1a}$, $R^{1b}$, $R^2$ and $R^3$ above. In particular, the hydrocarbon group represented by $R^8$ is preferably an alkyl group such as a $C_{1-6}$ alkyl group, and the substituent thereof is preferably carboxyl, $C_{1-6}$ alkoxy-carbonyl, or the like. $R^9$ is preferably a hydrogen atom or the like.

Examples of the "hydroxy group optionally having a substituent" represented by $R^{1a}$ include hydroxy groups having one group such as a hydrocarbon group optionally having a substituent, instead of a hydrogen atom of the hydroxy group.

Examples of the "hydroxy group optionally having a substituent" represented by $R^{1b}$, $R^2$, $R^3$ and $R^8$ include (1) a hydroxy group or (2) a hydroxy group having one group such as a hydrocarbon group optionally having a substituent, instead of a hydrogen atom of the hydroxy group.

The "hydrocarbon group optionally having a substituent" present in the hydroxy group is the same as the "hydrocarbon group optionally having a substituent" represented by $R^{1a}$, $R^{1b}$, $R^2$, $R^3$ and $R^8$ above.

With respect to Compound (Ia), the acyl group represented by $R^{1a}$, $R^{1b}$, $R^2$ and $R^3$ above is preferably ① a carboxyl group, ② a $C_{1-6}$ alkoxy-carbonyl group, ③ a carbamoyl group (or thiocarbamoyl group) which may be substituted by a $C_{1-6}$ alkyl group optionally having carboxyl or $C_{1-6}$ alkoxy-carbonyl, or the like.

In particular, $R^{1a}$ is preferably (1) a hydrogen atom, (2) a carboxyl group, (3) a $C_{1-6}$ alkoxy-carbonyl group, (4) a $C_{1-6}$ alkyl group which may be substituted by a group selected from the group consisting of (i) cyano, (ii) carboxyl, (iii) $C_{1-6}$ alkoxy-carbonyl and (iv) carbamoyl (or thiocarbamoyl) or (5) a carbamoyl group (or thiocarbamoyl group) which may be substituted by a $C_{1-6}$ alkyl group optionally having carboxyl or $C_{1-6}$ alkoxy-carbonyl, or the like.

With respect to Compound (Ib), when $R^{1b}$ is a hydrogen atom, the oxo group of the triazolo[4,3-b]pyridazine ring may be enolated, and the partial structural formula:

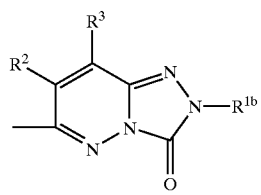

may represent any of the formula:

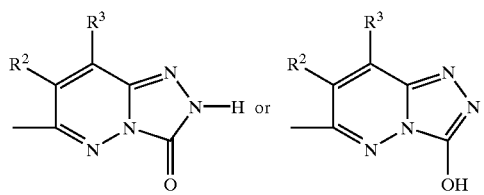

In particular, $R^{1b}$ is preferably (1) a hydrogen atom, (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl, or the like.

With respect to Formula (I) above, $R^2$ and $R^3$ are preferably a hydrogen atom.

In Formula (I) above, $R^7$ represents a hydrogen atom, a hydroxy group which may be substituted by a lower alkyl group or a carboxyl group.

Examples of the "lower alkyl group" of the "hydroxy group which may be substituted by a lower alkyl group" include $C_{1-6}$ alkyl groups such as methyl, ethyl, propyl, isopropyl, butyl, isobutyl, sec-butyl, tert-butyl, pentyl and hexyl.

$R^7$ is preferably a hydrogen atom or a hydroxy group, and a hydrogen atom is particularly preferred.

As Compound (I) of the present invention, the following are preferred:

COMPOUND (I)-I

Compound (I) wherein $R^{1a}$ is (1) a hydrogen atom, (2) a carboxyl group, (3) a $C_{1-6}$ alkoxy-carbonyl group, (4) a $C_{1-6}$ alkyl group which may be substituted by a group selected from the group consisting of (i) cyano, (ii) carboxyl, (iii) $C_{1-6}$ alkoxy-carbonyl and (iv) carbamoyl, or (5) a carbamoyl group which may be substituted by a $C_{1-6}$ alkyl group optionally having carboxyl or $C_{1-6}$ alkoxy-carbonyl;

$R^{1b}$ is (1) a hydrogen atom, or (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl;

$R^2$ and $R^3$ are a hydrogen atom;

$R^7$ is a hydrogen atom or a hydroxy group (particularly a hydrogen atom);

$Ar^1$ and $Ar^2$ are independently a phenyl group which may be substituted; Ring B is a ring represented by the formula:

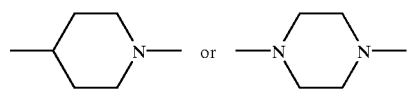

X is a bond or an oxygen atom;
Y is a group represented by the formula:

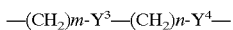

wherein $Y^3$ is a bond or —CH(OH)—, $Y^4$ is an oxygen atom, S or NH, and m and n are independently an integer from 0 to 6 (sum of m and n is not more than 6).

COMPOUND (I)-II

① 6-[6-[4-(diphenylmethoxy)piperidino]hexyloxy][1,2,4]triazolo[4,3-b]pyridazine or a salt thereof.

② 6-[6-[4-(diphenylmethoxy)piperidino]hexylamino][1,2,4]triazolo[4,3-b]pyridazine or a salt thereof.

③ 3-tert-butyl-6-[3-[4-(diphenylmethoxy)piperidino)propoxy][1,2,4]triazolo[4,3-b]pyridazine or a salt thereof.

④ 6-[3-[4-(diphenylmethoxy)piperidino]propylamino][1,2,4]triazolo[4,3-b]pyridazine-3-carboxylic acid or a salt thereof.

⑤ 6-[3-[4-(diphenylmethoxy)piperidino]propylamino][1,2,4]triazolo[4,3-b]pyridazin-3(2H)-one or a salt thereof.

⑥ Ethyl 2-[6-[3-[4-(diphenylmethoxy)piperidino]propylamino]-3-oxo[1,2,4]triazolo[4,3-b]pyridazin-2(3H)-yl]-2-methylpropionate or a salt thereof.

⑦ 2-[6-[3-[4-(diphenylmethoxy)piperidino]propylamino]-3-oxo[1,2,4]triazolo[4,3-b]pyridazin-2(3H)-yl]-2-methylpropionic acid or a salt thereof.

⑧ Pivaloyloxymethyl 2-[6-[3-[4-(diphenylmethoxy)piperidino]propylamino]-3-oxo[1,2,4]triazolo[4,3-b]pyridazin-2(3H)-yl]-2-methylpropionate or a salt thereof.

⑨ Pivaloyloxymethyl 2-[6-[3-[4-(diphenylmethoxy)piperidino]propoxy]-3-oxo[1,2,4]triazolo[4,3-b]pyridazin-2(3H)-yl]-2-methylpropionate or a salt thereof.

As Compound (Ia) of the present invention, the following are preferred:

COMPOUND (Ia)-I

Compound (Ia) wherein $Ar^1$ and $Ar^2$ are independently a phenyl group which may be substituted; Ring B is a ring represented by the formula:

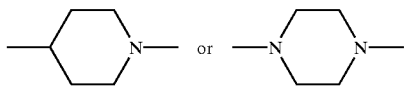

X is a bond or an oxygen atom;
Y is a group represented by the formula:

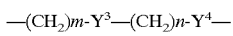

wherein $Y^3$ is a bond or —CH(OH)—, $Y^4$ is an oxygen atom, S or NH, and m and n are independently an integer from 0 to 4 (sum of m and n is not more than 6);

$R^{1a}$ is
(1) a hydrogen atom,
(2) a carboxyl group,
(3) a $C_{1-6}$ alkoxy-carbonyl group,
(4) a $C_{1-6}$ alkyl group which may be substituted by a group selected from the group consisting of (i) cyano, (ii) carboxyl, (iii) $C_{1-6}$ alkoxy-carbonyl and (iv) carbamoyl (or thiocarbamoyl), or
(5) a carbamoyl group (or thiocarbamoyl group) which may be substituted by a $C_{1-6}$ alkyl group optionally having carboxyl or $C_{1-6}$ alkoxy-carbonyl; and $R^2$, $R^3$ and $R^7$ are a hydrogen atom.

COMPOUND (Ia)-II

① 6-[6-(4-(diphenylmethoxy)piperidino]hexyloxy][1,2,4]triazolo[4,3-b]pyridazine or a salt thereof.

② 6-[6-[4-(diphenylmethoxy)piperidino]hexylamino][1,2,4]triazolo[4,3-b]pyridazine or a salt thereof.

③ 3-tert-butyl-6-[3-[4-(diphenylmethoxy)piperidino]propoxy][1,2,4]triazolo[4,3-b]pyridazine or a salt thereof.

④ 6-[3-[4-(diphenylmethoxy)piperidino]propylamino][1,2,4]triazolo[4,3-b]pyridazine-3-carboxylic acid or a salt thereof.

As Compound (Ib) of the present invention, the following are preferred:

COMPOUND (Ib)-I

Compound (Ib) wherein $Ar^1$ and $Ar^2$ are independently a phenyl group which may be substituted; Ring B is a ring represented by the formula:

X is an oxygen atom; Y is a group represented by the formula:

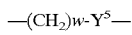

wherein w is an integer from 1 to 6, and $Y^5$ is an oxygen atom or NH; $R^{1b}$ is (1) a hydrogen atom, or (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl; and $R^2$, $R^3$ and $R^7$ are a hydrogen atom.

COMPOUND (Ib)-II

① 6-[3-[4-(diphenylmethoxy)piperidino]propylamino][1,2,4]triazolo[4,3-b]pyridazin-3(2H)-one or a salt thereof.

② Ethyl 2-[6-[3-[4-(diphenylmethoxy)piperidino)propylamino]-3-oxo[1,2,4]triazolo[4,3-b]pyridazin-2(3H)-yl]-2-methylpropionate or a salt thereof.

③ 2-[6-[3-[4-(diphenylmethoxy)piperidino]propylamino]-3-oxo[1,2,4]triazolo[4,3-b]pyridazin-2(3H)-yl]-2-methylpropionic acid or a salt thereof.

④ Pivaloyloxymethyl 2-[6-[3-[4-(diphenylmethoxy)piperidino]propylamino]-3-oxo[1,2,4]triazolo[4,3-b]pyridazin-2(3H)-yl]-2-methylpropionate or a salt thereof.

⑤ Pivaloyloxymethyl 2-[6-[3-[4-(diphenylmethoxy)piperidino]propoxy]-3-oxo[1,2,4]triazolo[4,3-b]pyridazin-2(3H)-yl)-2-methylpropionate or a salt thereof.

The pro-drug of Compound (I) of the present invention may be a compound which is converted into Compound (I) by a reaction with an enzyme, gastric acid, or the like under physiological conditions in the living body, i.e., a compound which is converted into Compound (I) upon enzymatic oxidation, reduction, hydrolysis, or the like, or a compound which is converted into Compound (I) upon hydrolysis or the like with gastric acid or the like.

Examples of the pro-drug of Compound (I) include compounds wherein the amino group of Compound (I) is acylated, alkylated, or phosphorylated (e.g., compounds wherein the amino group of Compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, or the like); compounds wherein the hydroxy group of Compound (I) is acylated, alkylated, phosphorylated, or borated (e.g., compounds wherein the hydroxy group of Compound (I) is acetylated, palmitoylated, propanoylated, pivaloylated, succinylated, fumarylated, alanylated, dimethylaminomethylcarbonylated, or the like); and compounds wherein the carboxyl group of Compound (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, methyl-amidated, or the like. These compounds can be produced by per se known methods from Compound (I).

In addition, the pro-drug of Compound (I) of the present invention may be a compound which is converted into Compound (I) under physiological conditions as described in "Pharmaceutical Research and Development," Vol. 7 (Drug Design), pages 163–198, published in 1990 by Hirokawa Publishing Co. (Tokyo, Japan).

Methods for producing Compound (I) of the present invention or a salt thereof are described below.

(A) Of Compound (I) of the present invention or a salt thereof, Compound (Ia) or a salt thereof can be produced by reacting a compound represented by the formula:

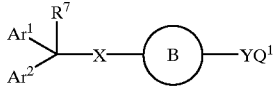

(IIa)

wherein $Q^1$ represents a leaving group; the other symbols have the same definitions as those shown above, or a salt thereof, with a compound represented by the formula:

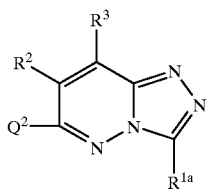

(IIIa)

wherein $Q^2$ represents a leaving group; the other symbols have the same definitions as those shown above, or a salt thereof.

Examples of the leaving group represented by $Q^1$ include alkali metals such as sodium and potassium. $Q^1$ may be a hydrogen atom.

Examples of the leaving group represented by $Q^2$ induce halogen atoms (e.g., chlorine atom, bromine atom, iodine atom), $C_{6-10}$ arylsulfonyloxy groups (e.g., benzenesulfonyloxy, p-tolylsulfonyloxy) and $C_{1-4}$ alkyl-sulfonyloxy groups (e.g., methanesulfonyloxy).

In this reaction, Compound (IIa) or a salt thereof is normally used at 1 to 5 mol, preferably 1 to 2 mol, per mol of Compound (IIIa) or a salt thereof. This condensation reaction is preferably carried out in the presence of a base.

Examples of the base include alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(B) Also, Compound (Ia) of the present invention or a salt thereof can be produced by reacting a compound represented by the formula:

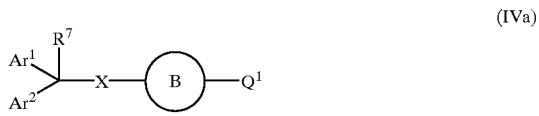

(IVa)

wherein the symbols have the same definitions as those shown above, or a salt thereof, with a compound represented by the formula:

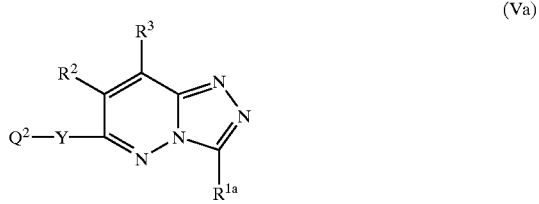

(Va)

wherein the symbols have the same definitions as those shown above, or a salt thereof.

In this reaction, Compound (IVa) or a salt thereof is normally used at 1 to 5 mol, preferably 1 to 2 mol, per mol of Compound (Va) or a salt thereof. This condensation reaction is preferably carried out in the presence of a base. Examples of the base include alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate.

In addition, this reaction can also be carried out in an inert solvent exemplified by alcohols such as methanol and ethanol; ethers such as dioxane and tetrahydrbfuran; aromatic hydrocarbons such as benzene, toluene and xylene; nitrites such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(C) Compound (Ia) of the present invention or a salt thereof can be produced by reacting a compound represented by the formula:

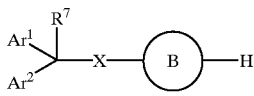
(VIa)

wherein the symbols have the same definitions as those shown above, or a salt thereof, with a compound represented by the formula:

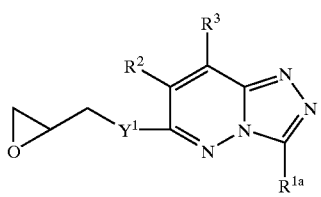
(VIIa)

wherein the symbols have the same definitions as those shown above, or a salt thereof.

In this reaction, Compound (VIa) or a salt thereof is normally used at 1 to 5 mol, preferably 1 to 2 mol, per mol of Compound (VIIa) or a salt thereof.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitrites such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(D) Also, Compound (Ia) of the present invention or a salt thereof can be produced by reacting a compound represented by the formula:

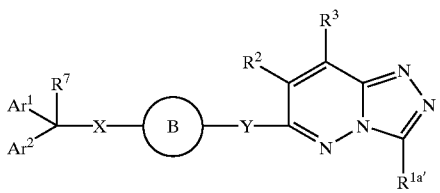
(Ia')

wherein $R^{1a'}$ is a cyano group, an alkoxycarbonyl group, a carboxyl group, a substituted carbamoyl group, or a $C_{1-6}$ alkyl group which may be substituted by cyano, alkoxycarbonyl, carboxyl, substituted carbamoyl, or the like; the other symbols have the same definitions as those shown above, or a salt thereof, with an acid or a base.

Examples of the alkoxycarbonyl group represented by $R^{1a}$ include $C_{1-6}$ alkoxy-carbonyl groups such as methoxycarbonyl, ethoxycarbonyl, propoxycarbonyl, and butoxycarbonyl.

Examples of the substituted carbamoyl group represented by $R^{1a'}$ include mono-lower alkyl-carbamoyl groups (e.g., mono-$C_{1-6}$ alkyl-carbamoyl groups such as methylcarbamoyl and ethylcarbamoyl), di-lower alkyl-carbamoyl groups (e.g., di-$C_{1-6}$ alkylcarbamoyl groups such as dimethylcarbamoyl and diethylcarbamoyl), and aryl-carbamoyl groups (e.g., $C_{6-10}$ aryl-carbamoyl groups such as phenylcarbamoyl and naphthylcarbamoyl).

Examples of the $C_{1-6}$ alkyl group represented by $R^{1a'}$ include methyl, ethyl, propyl, isopropyl, butyl, isobutyl, sec-butyl, tert-butyl, pentyl, and hexyl. The alkoxycarbonyl and substituted carbamoyl which is a substituent for this $C_{1-6}$ alkyl group is the same as the alkoxycarbonyl and substituted carbamoyl represented by $R^{1a'}$.

In this reaction, an acid or a base is normally used at 1 to 5 mol, preferably 1 to 2 mol, per mol of Compound (Ia') or a salt thereof.

Examples of the base used for this reaction include alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate.

Examples of the acid used for this reaction include inorganic acids such as hydrochloric acid, sulfuric acid and nitric acid.

In addition, this reaction can also be carried out in a solvent exemplified by water; alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

Compound (Ia) thus obtained can be converted into a salt by a conventional method. When Compound (Ia) is obtained as a salt, it can be converted into a free form or another salt by a conventional method. Compound (Ia) or a salt thereof thus obtained can be isolated and purified by known means such as solvent extraction, liquid-liquid transformation, re-dissolution, salting-out, crystallization, recrystallization and chromatography. When Compound (Ia) or a salt thereof contains optical isomers, it can be resolved into the R- and S-configurations by an ordinary means of optical resolution.

Methods for producing Starting Compounds (IIa) through (VIIIa) or salts thereof which are used to produce Compound (Ia) of the present invention or a salt thereof are described below.

Salts of these Compounds (Ia) through (VIIIa) include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, methanesulfonic acid, benzenesulfonic acid). Provided that these compounds have an acidic group such as that of a carboxylic acid, as a substituent, the acidic group may form a salt with an inorganic base (e.g., alkali metal or alkaline earth metal such as sodium, potassium, calcium or magnesium, or ammonia) or an organic base (e.g., tri-$C_{1-3}$ alkylamine such as triethylamine).

Starting Compounds (IIa) and (IVa) or salts thereof can, for example, be synthesized by the method described in the Journal of Medicinal Chemistry, Vol. 32, p. 583 (1989), or a modification thereof.

Starting Compound (IIIa) or a salt thereof can, for example, be synthesized by the method described in the Journal of the Pharmaceutical Society of Japan, Vol. 75, p. 1242 (1955), or a modification thereof.

Starting Compounds (Va) and (VIIa) or salts thereof can, for example, be synthesized by the methods described in Japanese Patent Unexamined Publication No. 223287/1991 etc., or modifications thereof.

Starting Compounds (VIa) or a salt thereof can, for example, be synthesized by the method described in the Journal of Medicinal Chemistry, Vol. 38, p. 2472 (1995), or a modification thereof.

Although these starting compound or salts thereof thus obtained can be isolated and purified by known means such as solvent extraction, liquid-liquid transformation, re-dissolution, salting-out, crystallization, recrystallization and chromatography, they may also be used as a starting material for the next process in the form of a reaction mixture as-is without isolation.

(A) On the other hand, Compound (Ib) of the present invention or a salt thereof can be produced by reacting a compound represented by the formula:

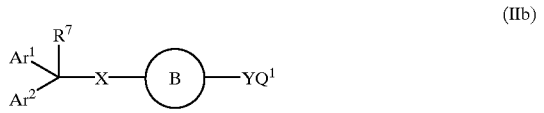

(IIb)

wherein the symbols have the same definitions as those shown above, or a salt thereof, with a compound represented by the formula:

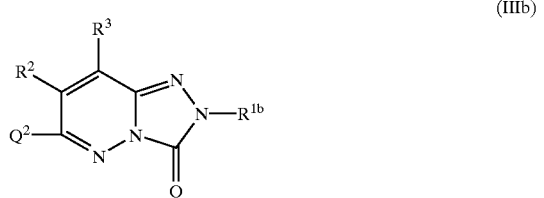

(IIIb)

wherein the symbols have the same definitions as those shown above, or a salt thereof.

In this reaction, Compound (IIb) or a salt thereof is normally used at 1 to 5 mol, preferably 1 to 2 mol, per mol of Compound (IIIb) or a salt thereof. This condensation reaction is preferably carried out in the presence of a base. Examples of the base include alkali metal hydrides such as sodium hydride and potassium hydride; alkali metal alkoxides such as sodium methoxide and sodium ethoxide.; alkali metal hydroxides such as sodium hydroxide and potassium hydroxide; and alkali metal carbonates such as sodium carbonate and potassium carbonate.

In addition, this reaction can also be carried out in a solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(B) Also, Compound (Ib) of the present invention or a salt thereof can be produced by reacting a compound represented by the formula:

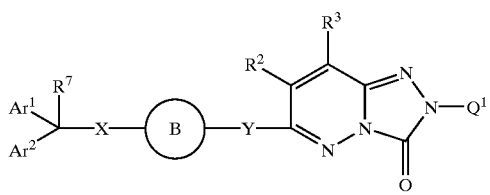

(IVb)

wherein the symbols have the same definitions as those shown above, or a salt thereof, with a compound represented by the formula:

$$Q^2—R^{1b}$$ (Vb)

wherein the symbols have the same definitions as those shown above, or a salt thereof.

In this reaction, Compound (Vb) or a salt, thereof is normally used at 1 to 5 mol, preferably 1 to 2 mol, per mol of Compound (IVb) or a salt thereof. This condensation reaction is preferably carried out in the presence of a base. Examples of the base include alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(C) Also, Compound (Ib) of the present invention or a salt thereof can be produced by reacting a compound represented by the formula:

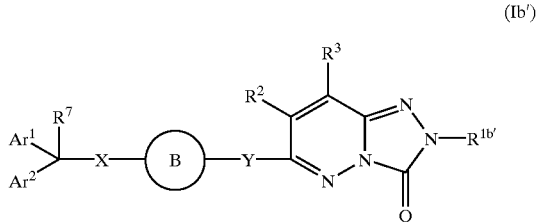

(Ib')

wherein $R^{1b'}$ is a cyano group, an alkoxycarbonyl group, a carboxyl group, a substituted carbambyl group, or a $C_{1-6}$ alkyl group which may be substituted by cyano, alkoxycarbonyl, carboxyl, substituted carbamoyl, or the like; the other symbols have the same definitions as those shown above, or a salt thereof, with an acid or a base. Each group represented by $R^{1b'}$ has the same definition as that represented by $R^{1a'}$.

In this reaction, an acid or a base is normally used at 1 to 5 mol, preferably 1 to 2 mol, per mol of Compound (Ib') or a salt thereof.

Examples of the base used for this reaction include alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate.

Examples of the acid used for this reaction include inorganic acids such as hydrochloric acid, sulfuric acid and nitric acid.

In addition, this reaction can also be carried out in an inert solvent exemplified by water; alcohols such as methanol and ethanol; ethers such as dioxane and tetrahydrofuran; aromatic hydrocarbons such as benzene, toluene and xylene; nitrites such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

Compound (Ib) thus obtained can be converted into a salt by a conventional method. When Compound (Ib) is obtained as a salt, it can be converted into a free form or another salt by a conventional method. Compound (Ib) or a salt thereof thus obtained can be isolated and purified by known means such as solvent extraction, liquid-liquid transformation, re-dissolution, salting-out, crystallization, recrystallization and chromatography. When Compound (Ib) or a salt thereof contains optical isomers, they can be resolved into the R- and S-configurations by an ordinary means of optical resolution.

Methods for producing Starting Compounds (IIb) and (IIIb) or salts thereof which are used to produce Compound (Ib) of the present invention or a salt thereof are described below.

Salts of these Compounds (Ib) through (IIIb) include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, methanesulfonic acid, benzenesulfonic acid). Provided that these compounds have an acidic group such as that of a carboxylic acid, as a substituent, the acidic group may form a salt with an inorganic base (e.g., alkali metal or alkaline earth metal such as sodium, potassium, calcium or magnesium, or ammonia) or an organic base (e.g., tri-$C_{1-3}$ alkylamine such as triethylamine).

Starting Compound (IIb) or a salt thereof can, for example, be synthesized by the method described in the Journal of Medicinal Chemistry, Vol. 32, p. 583 (1989), or a modification thereof.

Starting Compound (IIIb) or a salt thereof can, for example, be synthesized by the method described in the Journal of Heterocyclic Chemistry, Vol. 13, p. 673 (1976), or a modification thereof.

Although these starting compound or salts thereof thus obtained can be isolated and purified by known means such as solvent extraction, liquid-liquid transformation, re-dissolution, salting-out, crystallization, recrystallization and chromatography, they may also be used as a starting material for the next process in the form of a reaction mixture as-is without isolation.

Also, when the starting compound used in each of the above-mentioned reactions for producing Compounds (Ia) and (Ib) of the present invention or salts thereof or for synthesizing starting compounds has an amino group, a carboxyl group or a hydroxyl group as a substituent, these substituents may have a protective group in common use in peptide chemistry etc. incorporated therein; the desired compound can be obtained by removing, as appropriate, the protective group after completion of the reaction.

Amino group-protecting groups include, for example, formyl, $C_{1-6}$ alkylcarbonyls optionally having a substituent (e.g., acetyl, ethylcarbonyl), phenylcarbonyl, $C_{1-6}$ alkyl-oxycarbonyls (e.g., methoxycarbonyl, ethoxycarbonyl), phenyloxycarbonyl, $C_{7-10}$ aralkyl-carbonyls (e.g., benzylcarbonyl), trityl, phthaloyl and N,N-dimethylaminomethylene. Substituents for these groups include halogen atoms (e.g., fluorine, chlorine, bromine, iodine), $C_{1-6}$ alkyl-carbonyls (e.g., mrethylcarbonyl, ethylcarbonyl, butylcarbonyl) and nitro groups, the number of substituents being about 1 to 3.

Carboxyl group-protecting groups include, for example, $C_{1-6}$ alkyls optionally having a substituent (e.g., methyl, ethyl, n-propyl, i-propyl, n-butyl, tert-butyl), phenyl, trityl and silyl. Substituents for these groups include halogen atoms (e.g., fluorine, chlorine, bromine, iodine), formyl, $C_{1-6}$ alkyl-carbonyls (e.g., acetyl, ethylcarbonyl, butylcarbonyl) and nitro groups, the number of substituents being about 1 to 3.

Hydroxy group-protecting groups include, for example, $C_{1-6}$ alkyls optionally having a substituent (e.g., methyl, ethyl, n-propyl, i-propyl, n-butyl, tert-butyl), phenyl, $C_{7-10}$ aralkyls (e.g., benzyl), formyl, $C_{1-6}$ alkyl-carbonyls (e.g., acetyl, ethylcarbonyl), phenyloxycarbonyl, benzoyl, $C_{7-10}$ aralkyl-carbonyls (e.g., benzylcarbonyl), pyranyl, furanyl and silyl. Substituents for these groups include halogen atoms (e.g., fluorine, chlorine, bromine, iodine), $C_{1-6}$ alkyls (e.g., methyl, ethyl, n-propyl), phenyl, $C_{7-10}$ aralkyls (e.g., benzyl) and nitro groups, the number of substituents being about 1 to 4.

The protecting groups can be removed by commonly known methods or modifications thereof, including treatments with acids, bases, reducing agents, ultraviolet rays, hydrazine, phenylhydrazine, sodium N-methyldithiocarbamate, tetrabutylammonium fluoride, palladium acetate, etc.

The compound (I) of the present invention or a salt thereof (including a pro-drug of the compound (I)) can be safely used as an anti-allergic agent in mammals (e.g., humans, mice, dogs, rats, bovines), because it exhibits excellent anti-allergic, anti-histaminic, anti-inflammatory, anti-PAF (platelet-activating factor) or eosinophil chemotaxis-inhibiting activity, etc., with low toxicity (acute toxicity: $LD_{50}$>2 g/kg).

Furthermore, the compound (I) of the present invention or a salt thereof exhibits an eosinophil chemotaxis-inhibiting activity as well as an anti-histaminic activity, and can be used to treat or prevent allergic diseases such as chronic urticaria and other forms of urticaria (e.g., acute urticaria), atopic dermatitis, allergic rhinitis, allergic conjunctivitis, and hypersensitivity pneumonitis; dermal diseases (especially allergic dermal diseases) such as itching, herpetic dermatitis, eczematous dermatitis, contact dermatitis, prurigo, and psoriasis; respiratory diseases such as eosinophilic pneumonia (PIE syndrome), chronic obstructive pulmonary disease (COPD), and asthma; increased nasal cavity resistance, sneezing, nasal discharge, pollenosis, upper airway hypersensitivity, etc., in the mammals mentioned above. In particular, Compound (I) or a salt thereof is used as a preventive or therapeutic agent for asthma, allergic conjunctivitis, allergic rhinitis, chronic urticaria, atopic dermatitis, or the like. The route of administration may be oral or non-oral.

Also, the preparation for the present invention may contain as active ingredients pharmaceutical components other than the compound (I) or a salt therof. Such pharmaceutically active components include, for example, anti-asthmatics (e.g., theiphylline, procaterol, ketotifen, azelastine, seratrodast), anti-allergic agents (g.g., ketotifen, terfenadine, azelastine, epinastine), anti-inflammatory agents (e.g., cefixime, cefdinir, ofloxacin, tosufloxacin) and antifungal agents (e.g., fluconazole, itraconazole). These components are not subject to limitation, as long as the object of the present invention is accomplished, and may be used in appropriate mixing ratios. Useful dosage forms include, for example, tablets (including sugar-coated tablets and film-coated tablets), pills, capsules (including microcapsules), granules, fine granules, powders, syrups, emulsions, suspensions, injectable preparations, inhalants, ointments, eyedrops, aerosols, eye ointments, plasters, suppositories, troches, poultices, and liniments, these preparations are prepared by conventional methods (e.g., methods described in the Japanese Pharmacopoeia).

In the preparation of the present invention, the content of the compound (I) or a salt thereof is normally about 0.01 to 100% by weight, preferably 0.1 to 50% by weight, and more preferably 0.5 to 20% by weight, relative to the entire preparation, depending on the form of the preparation.

Specifically, tablets can be produced by granulating a pharmaceutical as-is, or in a uniform mixture with an excipient, a binder, a disintegrating agent or other appropriate additives, by an appropriate method, then adding lubricants etc., and subjecting the mixture to compressive shaping, or by subjecting to direct compressive shaping a pharmaceutical as-is, or in a uniform mixture with an excipient, a binder, a disintegrating agent or other appropriate additives, or subjecting to compressive shaping previously prepared granules as-is, or in a uniform mixture with appropriate additives. These tablets may incorporate coloring agents, correctives etc. as necessary, and may be coated with appropriate coating agents.

Injectable preparations can be produced by dissolving, suspending or emulsifying a given amount of a pharmaceutical in an aqueous solvent such as water for injection, physiological saline or Ringer's solution, or a non-aqueous solvent such as a vegetable oil, and diluting to a given amount, or transferring a given amount of a pharmaceutical into a container for injection and sealing the container.

Examples of the carriers for oral preparations include substances in common use in pharmaceutical production, such as starch, mannitol, crystalline cellulose and carboxymethyl cellulose sodium. Examples of the carriers for injectable preparations include distilled water, physiological saline, glucose solutions and transfusions. Other additives in common use for pharmaceutical production can also be added, as appropriate.

Depending on patient age, body weight, symptoms, route and frequency of administration and other factors, the daily dose of these preparations is normally 0.1 to 100 mg/kg, preferably 1 to 50 mg/kg, and more preferably 1 to 10 mg/kg, based on daily dose of active ingredient (Compound (I) or a salt thereof), once or in two portions daily for each asthmatic adult.

The present invention is hereinafter described in more detail by means of the following reference examples, working examples (Examples), formulation examples and experimental examples, which are not to be construed as limitative.

In the working examples and reference examples below, the fraction containing the desired product was detected by observation via TLC (thin-layer chromatography).

In the TLC observation, 60F254, produced by Merck, was used as a TLC plate, with a UV detector as a means of detection.

The silica gel used for column chromatography was Merck Silica Gel 60 (70–230 mesh).

The abbreviations used herein have the definitions shown below.

J: Coupling constant
s: Singlet
t: Triplet
m: Multiplet
Hz: Hertz
d: Doublet
q: Quartet
$^1$H-NMR: Proton nuclear magnetic resonance
$CDCl_3$: Deuterated chloroform
v/v: Volume/volume
%: % by weight COMPOUND (Ia):

REFERENCE EXAMPLE 1a

Production of 3-tert-Butyl-6-chloro[1,2,4]triazolo[4,3-b]pyridazine 2.78 g of N'-(6-chloro-3-pyridazinyl)-2,2-dimethylpropionohydrazide was stirred under heating at an external temperature of 170° C. for 10 minutes. After cooling, the reaction mixture was dissolved in ethyl acetate, subjected to silica gel column chromatography, and eluted with ethyl acetate. The desired fraction was collected and concentrated under reduced pressure; the precipitated crystal was washed with hexane and dried to yield 2.38 g of the title compound.

Melting point: 150–152° C.; Elemental analysis (for $C_9H_{11}N_4Cl$): Calculated (%): C, 51.31; H, 5.26; N, 26.60; Found (%): C, 51.36; H, 5.17; N, 26.62.

REFERENCE EXAMPLE 2a

Production of 6-(2-Oxiranylmethoxy)[1,2,4]triazolo[4,3-b]pyridazine 12.0 g of 2-oxiranylmethanol and 2.50 g of 6-chloro[1,2,4]triazolo[4,3-b]pyridazine were dissolved in 40 ml of N,N-dimethylformamide; under ice cooling, 713 mg of 60% oily sodium hydride was added, followed by stirring at room temperature for 30 minutes. After cold saline was added, the reaction mixture was extracted with ethyl acetate-tetrahydrofuran (1:1) and dried over magnesium sulfate. After concentration under reduced pressure, the residue was subjected to silica gel column chromatography and eluted with ethyl acetate-methanol (10:1). The desired fraction was collected and concentrated under reduced pressure; the precipitated crystal was washed with diethyl ether and dried to yield 1.02 g of the title compound.

$^1$H-NMR ($CDCl_3$) δ ppm: 2.78 (1H, dd, J=2.5, 4.7 Hz), 2.96 (1H, t, J=4.4 Hz), 3.47–3.89 (1H, m), 4.20 (1H, dd, J=6.6, 12.0 Hz), 4.70 (1H, dd, J=2.9, 12.1 Hz), 6.87 (1H, d, J=10.0 Hz), 8.01 (1H, d, J=9.8 Hz), 8.86 (1H, s).

REFERENCE EXAMPLE 3a

Production of 2-(6-Chloro[1,2,4]triazolo[4,3-b]pyridazin-3-yl)-2-methylpropionitrile Process A: Production of N'-(6-Chloro-3-pyridazinyl)-2-cyano-2-methylpropionohydrazide 4.15 g of 2-cyano-2-methylpropionic acid was dissolved in 40 ml of tetrahydrofuran; under ice cooling, 5.95 g of N,N'-carbonyldiimidazole was added. After stirring at room temperature for 50 minutes, 5.05 g of (6-chloro-3-pyridazinyl)hydrazine was added under ice cooling, followed by stirring at room temperature for 40 minutes. After saline was added, the reaction mixture was extracted with ethyl acetate-tetrahydrofuran (1:1) and dried over magnesium sulfate. After concentration under reduced pressure, the residue was subjected to silica gel column chromatography and eluted with ethyl acetate. The desired fraction was collected and concentrated under reduced pressure; the precipitated crystal was washed with diethyl ether and dried to yield 7.04 g of the title compound.

$^1$H-NMR (CDCl$_3$) δ ppm: 1.62 (6H, s), 7.00 (1H, d, J=9.4 Hz), 7.51 (1H, d, J=9.2 Hz), 9.22 (1H, s), 10.4 (1H, s).

Process B:

6.43 g of N'-(6-chloro-3-pyridazinyl)-2-cyano-2-methylpropionohydrazide was stirred under heating at an external temperature of 160° C. for 20 minutes. After cooling, water was added; the reaction mixture was extracted with ethyl acetate-tetrahydrofuran (1:1), washed with saturated saline, and dried over magnesium sulfate. After concentration under reduced pressure, the residue was subjected to silica gel column chromatography and eluted with ethyl acetate. The desired fraction was collected and concentrated under reduced pressure; the precipitated crystal was washed with diethyl ether and dried to yield 3.65 g of the title compound.

Melting point: 153–155° C.; Elemental analysis (for C$_9$H$_8$N$_5$Cl): Calculated (%): C, 48.77; H, 3.64; N, 31.60; Found (%): C, 48.69; H, 3.69; N, 31.55.

REFERENCE EXAMPLE 4a

Production of Ethyl 6-Chloro[1,2,4]triazolo[4,3-b]pyridazine-3-carboxylate 7.04 g of (6-chloro-3-pyridazinyl)hydrazine was dissolved in 70 ml of ethanol; 8.6 ml of diethyl oxalate was added, followed by stirring at room temperature for 16 hours and subsequent refluxing under heating for 1 day. After cooling, the precipitated crystal was washed with diethyl ether and dried to yield 7.32 g of the title compound.

$^1$H-NMR (CDCl$_3$) δ ppm: 1.52 (3H, t, J=7.0 Hz), 4.61 (2H, q, J=7.0 Hz), 7.33 (1H, d, J=9.6 Hz), 8.24 (1H, d, J=10.0 Hz).

REFERENCE EXAMPLE 5a

Production of N-(6-Chloro[1,2,4]triazolo[4,3-b]pyridazine-3-carbonyl)-2,2-dimethylglycine Ethyl Ester 329 mg of (6-chloro-3-pyridazinyl)hydrazine was dissolved in 3 ml of ethanol; 206 mg of N-(ethyloxalyl)-2,2-dimethylglycine ethyl ester was added. After stirring at room temperature for 15 hours, the reaction mixture was refluxed under heating for 16 hours; the ethanol was distilled off, followed by stirring under heating at an external temperature of 110° C. for 5 hours. After cooling, saline was added; the reaction mixture was extracted with ethyl acetate-tetrahydrofuran (1:1) and dried over sodium sulfate. After concentration under reduced pressure, the residue was subjected to silica gel column chromatography and eluted with ethyl acetate. The desired fraction was collected and concentrated under reduced pressure; the precipitated crystal was washed with diethyl ether-hexane (1:1) and dried to yield 154 mg of the title compound.

Melting point: 132–133° C.; Elemental analysis (for C$_{12}$H$_{14}$N$_5$O$_3$Cl): Calculated (%): C, 46.24; H, 4.53; N, 22.47; Found (%): C, 46.27; H, 4.58; N, 22.54.

REFERENCE EXAMPLE 6a

Production of N-(6-Chloro[1,2,4]triazolo[4,3-b]pyridazine-3-carbonyl)glycine Ethyl Ester 4.05 g of (6-chloro-3-pyridazinyl)hydrazine was dissolved in 20 ml of ethanol; 5.69 g of N-(ethyloxalyl)glycine ethyl ester was added; while the ethanol was evaporated, the reaction mixture was refluxed under heating for 2 days. After cooling, water was added; the reaction mixture was extracted with ethyl acetate-tetrahydrofuran (1:1), washed with saturated saline, and dried over magnesium sulfate. After concentration under reduced pressure, the residue was subjected to silica gel column chromatography and eluted with ethyl acetate. The desired fraction was collected and concentrated under reduced pressure; the precipitated crystal was washed with diethyl ether and dried to yield 1.99 g of the title compound.

Melting point: 133–134° C.; Elemental analysis (for C$_{10}$H$_{10}$N$_5$O$_3$Cl): Calculated (%): C, 42.34; H, 3.55; N, 24.69; Found (%): C, 42.47; H, 3.44; N, 24.88.

EXAMPLE 1a

Production of 6-[3-[4-(Diphenylmethyl)-1-piperazinyl]propoxy][1,2,4]triazolo[4,3-b]pyridazine 0.311 g of 4-(diphenylmethyl)-1-piperazinepropanol was dissolved in 5 ml of N,N-dimethylformamide; 0.048 g of 60% oily sodium hydride was added; the reaction mixture was stirred in an oil bath (60° C.) for 30 minutes. After cooling, 0.232 g of 6-chloro[1,2,4]triazolo[4,3-b]pyridazine was added; the reaction mixture was stirred in an oil bath. (bath temperature 60° C.) for 40 minutes. After cooling, ice water was added; the reaction mixture was extracted with ethyl acetate; the extract was washed with saline and dried over magnesium sulfate. After concentration under reduced pressure, the residue was subjected to silica gel column chromatography and eluted with ethyl acetate-methanol-triethylamine (90:10:1). The desired fraction was collected and concentrated; the crystal obtained was filtered, washed with ethyl ether, and dried, to yield 0.339 g of the title compound.

Melting point: 132–134° C.; Elemental analysis (for C$_{25}$H$_{28}$N$_6$O): Calculated (%): C, 70.07; H, 6.59; N, 19.61; Found (%): C, 69.71; H, 6.55; N, 19.48.

EXAMPLE 2a

Production of 6-[3-[4-(Diphenylmethyl)-1-piperazinyl]propylthio][1,2,4]triazolo[4,3-b]pyridazine Process A: 6-(3-Chloropropylthio)[1,2,4]triazolo[4,3-b]pyridazine 7.8 ml of methyl 3-mercaptopropionate was dissolved in 80 ml of methanol; 30 ml of a 2 N solution of sodium methoxide in methanol and 3.10 g of 6-chloro[1,2,4]triazolo[4,3 b]pyridazine were added, followed by refluxing under heating for 40 minutes. After cooling, the reaction mixture was concentrated under reduced pressure; to the residue, ethyl acetate was added; the precipitated crystal was collected, washed with ethyl acetate, and suspended in 80 ml of tetrahydrofuran; 3.95 ml of 1-bromo-3-chloropropane was added; followed by refluxing under heating for 2.5 hours. After cooling, ice water was added; the reaction mixture was extracted with ethyl acetate; the extract was washed with saline and dried over magnesium sulfate. After concentration under reduced pressure, the residue was subjected to silica gel column chromatography and eluted with ethyl acetate. The desired fraction was collected and concentrated; the crystal obtained was collected to yield 3.95 g of the title compound.

Melting point: 79–80° C.; Elemental analysis (for $C_8H_9N_4SCl$): Calculated (%): C, 42.01; H, 3.97; N, 24.50; Found (%): C, 41.92; H, 3.72; N, 24.64.

Process B:

0.458 g of 6-(3-chloropropylthio)[1,2,4]triazolo[4,3-b]pyridazine and 0.505 g of 1-(diphenylmethyl)piperazine were dissolved in 15 ml of acetonitrile; 0.447 g of sodium iodide and 0.277 g of potassium carbonate were added, followed by refluxing under heating for 6 hours. After cooling, ice water was added; the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol (90:10). The desired fraction was collected and concentrated; the crystal obtained was recrystallized from ethyl acetate to yield 0.335 g of the title compound.

Melting point: 143–144° C.; Elemental analysis (for $C_{25}H_{28}N_6S$): Calculated (%): C, 67.54; H, 6.35; N, 18.90; Found (%): C, 67.34; H, 6.40; N, 18.91.

EXAMPLE 3a

Production of 6-[3-[4-(Diphenylmethoxy)piperidino]propylthio][1,2,4]triazolo[4,3-b]pyridazine Fumarate (2:3)

0.458 g of 6-(3-chloropropylthio)[1,2,4]triazolo[4,3-b]pyridazine and 0.534 g of 4-(diphenylmethoxy)piperidine were dissolved in 15 ml of acetonitrile; 0.447 g of sodium iodide and 0.277 g of potassium carbonate were added, followed by refluxing under heating for 15 hours. After cooling, ice water was added; the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (90:10:1). The desired fraction was collected and concentrated; the residue was dissolved in 20 ml of ethanol; 0.185 g of fumaric acid was added. The precipitated crystal was collected, washed with ethanol, and dried, to yield 0.396 g of the title compound.

Melting point: 148–150° C.; Elemental analysis (for $C_{26}H_{29}N_5OS \cdot 1.5(C_4H_4O_4)$): Calculated (%): C, 60.65; H, 5.57; N, 11.05; Found (%): C, 60.72; H, 5.44; N, 11.19.

EXAMPLE 4a

Production of 6-[3-(4-(Diphenylmethoxy)piperidino]propylamino][1,2,4]triazolo[4,3-b]pyridazine 0.464 g of 6-chloro[1,2,4]triazolo[4,3-b]pyridazine and 1.26 g of 4-(diphenylmethoxy)-1-piperidinepropanamine were suspended in 20 ml of 1-butanol; 0.62 ml of N-ethyldiisopropylamine was added, followed by refluxing under heating for 12 hours. After ice water and sodium hydrogen carbonate were added, the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (90:10:1). The desired fraction was collected and concentrated; the crystal obtained was washed with ethyl acetate and dried to yield 0.648 g of the title compound.

Melting point: 167–168° C.; Elemental analysis (for $C_{26}H_{30}N_6O$): Calculated (%): C, 70.56; H, 6.83; N, 18.99; Found (%): C, 70.21; H, 6.75; N, 19.06.

EXAMPLE 5a

Production of 6-[4-[4-(Diphenylmethoxy)piperidino]butylamino][1,2,4]triazolo[4,3-b]pyridazine 1.15 g of 4-(diphenylmethoxy)-1-piperidinebutanamine and 578 mg of 6-chloro[1,2,4]triazolo[4,3-b]pyridazine were dissolved in 20 ml of 1-butanol; 1.17 ml of N-ethyldiisopropylamine was added, followed by refluxing under heating for 14 hours. After cooling, ethyl acetate was added; the reaction mixture was washed with aqueous sodium bicarbonate and saturated saline and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the residue was crystallized from ethyl acetate and dried to yield 611 mg of the title compound.

Melting point: 145–146° C.; Elemental analysis, (for $C_{27}H_{32}N_6O$): Calculated (%): C, 71.03; H, 7.06; N, 18.41; Found (%): C, 70.95; H, 7.02; N, 18.73.

EXAMPLE 6a

Production of 6-(2-[4-(Diphenylmethoxy)piperidino]ethoxy)[1,2,4]triazolo[4,3-b]pyridazine 610 mg of 4-(diphenylmethoxy)-1-piperidine ethanol was dissolved in 15 ml of tetrahydrofuran; 207 mg of sodium tert-butoxide was added; the reaction mixture was stirred at an external temperature of 60° C. for 40 minutes. After cooling, 303 mg of 6-chloro,1,2,4]triazolo[4,3-b]pyridazine was added, followed by refluxing under heating for 8 hours. After cooling, water was added, and the mixture was extracted with ethyl acetate, washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the residue was crystallized from small amounts of ethyl acetate and diethyl ether, washed with diethyl ether, and dried, to yield 449 mg of the title compound.

Melting point: 149–150° C.; Elemental analysis (for $C_{25}H_{27}N_5O_2$): Calculated (%): C, 69.91; H, 6.34; N, 16.31; Found (%): C, 69.91; H, 6.08; N, 16.31.

EXAMPLE 7a

Production of 6-[6-[4-(Diphenylmethoxy)piperidino]hexyloxy][1,2,4]triazolo[4,3-b]pyridazine Fumarate 825 mg of 4-(diphenylmethoxy)-1-piperidinehexanol was dissolved in 13 ml of tetrahydrofuran; 108 mg of sodium hydride (60% in oil) was added, followed by refluxing under heating for 1.5 hours. After cooling, 347 mg of 6-chloro[1,2,4]triazolo[4,3-b]pyridazine was added, followed by refluxing under heating for 2 hours. After cooling, water was added; the reaction mixture was extracted with ethyl acetate, washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 940 mg of the residue was dissolved in ethanol; a solution of 225 mg of fumaric acid in ethanol was added, followed by concentration under reduced pressure. The residue was crystallized from ethanol-ethyl acetate (1:5), washed with ethyl acetate, and dried, to yield 939 mg of the title compound.

$^1$H-NMR (CDCl$_3$) δ ppm: 1.30–1.55 (4H, m), 1.65–1.85 (4H, m), 1.85–2.20 (4H, m), 2.80–3.35 (5H, m), 3.73 (1H, brs), 4.27 (2H, t, J 6.4 Hz), 5.44 (1H,s), 6.76(2H, S), 6.78 (1H, d, J=9.6 Hz), 7.25–7.35 (10H, m), 7.94 (1H, d, J=9.8 Hz), 8.87 (1H, s). Melting point: 144–146° C.; Elemental analysis (for C$_{33}$H$_{39}$N$_5$O$_6$): Calculated (%): C, 65.87; H, 6.53; N, 11.64; Found (%): C, 65.81; H, 6.48; N, 10.87.

EXAMPLE 8a

Production of 6-[6-[4-(Diphenylmethyl)-1-piperazinyl]hexyloxy][1,2,4]triazolo[4,3-b]pyridazine fumarate 529 mg of 4-(diphenylmethyl)-1-piperazinehexanol was dissolved in 8 ml of tetrahydrofuran; 90 mg of sodium hydride (60% in oil) was added, followed by stirring for 1 hour. After cooling, 232 mg of 6-chloro[1,2,4]triazolo[4,3-b]pyridazine was added, followed by refluxing under heating for 2 hours. After cooling, water was added; the reaction mixture was extracted with ethyl acetate, washed with saturated saline, and dried over magnesium sulfate. After concentration under reduced pressure, the residue was subjected to silica gel column chromatography and eluted with ethyl acetate-methanol (10:1). The desired fraction was collected and concentrated under reduced pressure; 320 mg of the residue was dissolved in ethanol; a solution of 71 mg of fumaric acid in ethanol was added, followed by concentration under reduced pressure residue was crystallized from ethanol-ethyl acetate-diethyl ether (1:2:2), washed with diethyl ether, and dried, to yield 113 mg of the title compound.

Melting point: 162–163° C.; Elemental analysis (for C$_{32}$H$_{38}$N$_6$O$_5$): Calculated (%): C, 65.51; H, 6.53; N, 14.32; Found (%): C, 65.12; H, 6.41; N, 14.10.

EXAMPLE 9a

Production of 6-[3-[4-(Diphenylmethoxy)piperidino]propoxy][1,2,4]triazolo[4,3-b]pyridazine fumarate 730 mg of 4-(diphenylmethoxy)-1-piperidinepropanol was dissolved in 17 ml of tetrahydrofuran; 237 mg of sodium tert-butoxide was added, followed by stirring at an external temperature of 60° C. for 30 minutes. After cooling, 347 mg of 6-chloro[1,2,4]triazolo[4,3-b]pyridazine was added, followed by refluxing under heating for 6 hours. After cooling, saline was added; the reaction mixture was extracted with ethyl acetate and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 470 mg of the residue was dissolved in ethanol; a solution of 123 mg of fumaric acid in ethanol was added, followed by concentration under reduced pressure. The residue was crystallized from ethanol-ethyl acetate (1:5) and dried to yield 341 mg of the title compound.

Melting point: 114–116° C.; Elemental analysis (for C$_{30}$H$_{33}$N$_5$O$_6$.0.5H$_2$O): Calculated (%): C, 63.37; H, 6.03; N, 12.32; Found (%): C, 63.61; H, 5.82; N, 12.34.

EXAMPLE 10a

Production of 6-[6-[4-(Diphenylmethoxy)piperidino]hexylamino][1,2,4]triazolo[4,3-b]pyridazine Process A: Production of 6-(6-Hydroxyhexylamino)[1,2,4]triazolo[4,3-b]pyridazine In 35 ml of ethanol, 3.55 g of 6-chloro[1,2,4]triazolo[4,3-b]pyridazine was suspended; 6.73 g of 6-aminohexanol was added, followed by refluxing under heating for 16 hours. After cooling, the reaction mixture was concentrated under reduced pressure; the residue was subjected to silica gel column chromatography and eluted with ethyl acetate-methanol-triethylamine (50:5:1). The desired fraction was collected and concentrated under reduced pressure; the precipitated crystal was washed with diethyl ether and,dried to yield 5.67 g of the title compound.

$^1$H-NMR (CDCl$_3$) δ ppm: 1.38–1.80 (8H, m), 3.11 (1H, q, J=6.4 Hz), 3.37 (2H, q, J=6.4 Hz), 3.67 (2H, t, J=6.1 Hz), 5.12 (1H, brs), 6.61 (1H, d, J=9.8 Hz), 7.78 (1H, d, J=10.0 Hz), 8.74 (1H, s).

Process B: Production of 6-[6-(Methanesulfonyloxy)hexylamino][1,2,4]triazolo[4,3-b]pyridazine 3.26 g of 6-(6-hydroxyhexylamino)[1,2,4]triazolo[4,3-b]pyridazine was suspended in 60 ml of tetrahydrofuran; 3.59 g of N-ethyldiisopropylamine and 3.17 g of methanesulfonyl chloride were added, followed by stirring at room temperature for 4 hours. Saline was added; the reaction mixture was extracted with ethyl acetate-tetrahydrofuran (1:1) and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the precipitated crystal was washed with diethyl ether, and dried, to yield 3.24 g of the title compound.

Melting point: 103–105° C.; Elemental analysis (for C$_{12}$H$_{19}$N$_5$O$_3$.0.3H$_2$O): Calculated (%): C, 45.21; H, 6.20; N, 21.97; Found (%): C, 45.15; H, 6.24; N, 21.60.

Process C:

810 mg of 6-[6-(methanesulfonyloxy)hexylamino][1,2,4]triazolo[4,3-b]pyridazine was dissolved in 15 ml of N,N-dimethylformamide; 829 mg of 4-(diphenylmethoxy)piperidine, 428 mg of potassium carbonate, and 515 mg of potassium iodide were added, followed by stirring at 60° C. for 4 hours. After cooling, saline was added; the reaction mixture was extracted with ethyl acetate and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the residue was crystallized from ethanol-ethyl acetate (1:5), washed with diethyl ether, recrystallized in the same manner, and dried, to yield 599 mg of the title compound.

Melting point: 124–127° C.; Elemental analysis (for C$_{29}$H$_{36}$N$_6$O.0.5H$_2$O): Calculated (%): C, 70.56; H, 7.55; N, 17.02; Found (%): C, 70.68; H, 7.29; N, 17.38.

EXAMPLE 11a

Production of 6-[6-[4-(Diphenylmethyl)-1-piperazinyl]hexylamino][1,2,4]triazolo[4,3-b]pyridazine 796 mg of 6-[6-(methanesulfonyloxy)hexylamino][1,2,4]triazolo[4,3-b]pyridazine was dissolved in 15 ml of N,N- dimethylformamide; 769 mg of 1-(diphenylmethyl) piperazine, 422 mg of potassium carbonate, and 506 mg of potassium iodide were added, followed by stirring at 60° C. for 4 hours. After cooling, saline was added; the reaction mixture was extracted with ethyl acetate and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the residue was crystallized from ethyl acetate, washed with diethyl ether, recrystallized in the same manner, and dried, to yield 353 mg of the title compound.

Melting point: 133–139° C.; Elemental analysis (for $C_{28}H_{35}N_7 \cdot 0.5H_2O$): Calculated (%): C, 70.26; H, 7.58; N, 20.48; Found (%): C, 70.12; H, 7.18; N, 20.60.

EXAMPLE 12a

Production of 3-tert-Butyl-6-[3-[4-(diphenylmethoxy)piperidino]propylamino][1,2,4]triazolo[4,3-b]pyridazine fumarate 854 mg of 4-(diphenylmethoxy)-1-piperidinepropanamine and 554 mg of 3-tert-butyl-6-chloro[1,2,4]triazolo[4,3-b]pyridazine were dissolved in 10 ml of 1-butanol; 0.91 ml of N-ethyldiisopropylamine was added, followed by refluxing under heating for 21 hours. After cooling, ethyl acetate was added; the reaction mixture was washed with saturated aqueous sodium bicarbonate and saturated saline and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 780 mg of the residue was dissolved in ethanol; a solution of 282 mg of fumaric acid in ethanol was added, followed by concentration under reduced pressure. The residue was crystallized from ethanol-ethyl acetate (1:5), washed with ethyl acetate, and dried, to yield 938 mg of the title compound.

$^1$H-NMR (DMSO-$d_6$) δ ppm: 1.49 (9H, s), 1.55–2.00 (6H, m), 2.30–2.68 (5H, m), 2.80–2.96 (2H, m), 3.20–3.35 (2H, m), 3.44 (1H, brs), 5.64 (1H,s), 6.58 (2H, s), 6.71 (1H, d, J=9.8 Hz), 7.20–7.45 (10H, m), 7.83 (1H, d, J=9.8 Hz). Melting point: 174–176° C.; Elemental analysis (for $C_{34}H_{42}N_6O_5 \cdot 1.5H_2O$): Calculated (%): C, 63.63; H, 7.07; N, 13.10; Found (%): C, 64.05; H, 6.58; N, 12.65.

EXAMPLE 13a

Production of 3-tert-Butyl-6-[3-[4-(diphenylmethoxy)piperidino]propoxy][1,2,4]triazolo[4.3-b]pyridazine 991 mg of 4-(diphenylmethoxy)-1-piperidinepropanol was dissolved in 20 ml of tetrahydrofuran; 322 mg of sodium tert-butoxide was added, followed by stirring at an external temperature of 60° C. for 2 hours. After cooling, 642 mg of 3-tert-butyl-6-chloro[1,2,4]triazolo[4,3-b]pyridazine was added, followed by refluxing under heating for 2 hours. After cooling, saline was added; the reaction mixture was extracted with ethyl acetate and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 1.26 g of the residue was dissolved in 3 ml of pyridine; 1.5 ml of acetic anhydride was added, followed by stirring at room temperature for 6 hours. After the reaction mixture was concentrated under reduced pressure, the residue was subjected to silica gel column chromatography and eluted with ethyl acetate-methanol-triethylamine (50:5:1). The desired fraction was collected and concentrated under reduced pressure; the residue crystallized from ethyl acetate-diethyl ether (1:1), washed with diethyl ether, and dried, to yield 500 mg of the title compound.

Melting point: 125–127° C.; Elemental analysis (for $C_{30}H_{37}N_5O_2$): Calculated (%): C, 72.12; H, 7.46; N, 14.02; Found (%): C, 71.93; H, 7.47; N, 14.18.

EXAMPLE 14a

Production of 6-[3-[4-(Diphenylmethoxy)piperidino]-2-hydroxypropoxy][1,2,4]triazolo[4,3-b]pyridazine fumarate 904 mg of 4-(diphenylmethoxy)piperidine and 650 mg of 6-(2-oxiranylmethoxy)[1,2,4]triazolo[4,3-b]pyridazine were suspended in 25 ml of ethanol, followed by stirring at room temperature for 14 hours, then at 60° C. for 2 hours. After cooling, the ethanol was distilled off; the residue was subjected to silica gel column chromatography and eluted with ethyl acetate-methanol-triethylamine (50:5:1). The desired fraction was collected and concentrated under reduced pressure; 1.11 g of the residue was dissolved in ethanol; a solution of 230 mg of fumaric acid in ethanol was added, followed by concentration under reduced pressure. The residue was crystallized from ethanol-ethyl acetate (1:5), washed with ethyl acetate-diethyl ether (1:1), and dried, to yield 591 mg of the title compound.

Melting point: 173–175° C.; Elemental analysis (for $C_{30}H_{33}N_5O_7$): Calculated (%): C, 61.63; H, 5.86; N, 11.98; Found (%): C, 61.87; H, 5.90; N, 12.24.

EXAMPLE 15a

Production of 6-[3-[4-(Diphenylmethyl)-1-piperazinyl]-2-hydroxypropoxy][1,2,4]triazolo[4,3-b]pyridazine 657 mg of 1-(diphenylmethyl)piperazine and 500 mg of 6-(2-oxylanylmethoxy)[1,2,4]triazolo[4,3-b]pyridazine were suspended in 20 ml of ethanol, followed by stirring at room temperature for 1 day. The precipitated crystal was collected by filtration and washed with diethyl ether. The filtrate was distilled under reduced pressure; the residue was subjected to silica gel column chromatography and eluted with ethyl acetate-methanol (10:1). The desired fraction was collected and concentrated under reduced pressure; the concentrate was combined with the previously collected crystal, crystallized from methanol-ethanol (1:5), washed with ethyl acetate-diethyl ether (1:1), and dried, to yield 269 mg of the title compound.

Melting point: 95–97° C.; Elemental analysis (for $C_{25}H_{28}N_6O_2$): Calculated (%): C, 63.68; H, 6.63; N, 17.82; Found (%): C, 64.05; H, 6.53; N, 17.76.

EXAMPLE 16a

Production of 2-[6-[3-[4-(Diphenylmethoxy)piperidino]propoxy][1,2,4]triazolo[4,3-b]pyridazin-3-yl]-2-methylpropionitrile Hydrochloride 6.55 g of 4-(diphenylmethoxy)-1-piperidinepropanol was dissolved in 100 ml of tetrahydrofuran; 2.12 g of sodium tert-butoxide was added, followed by stirring at an external temperature of 60° C. for 40 minutes. After cooling, 4.86 g of 2-[6-chloro[1,2,4]triazolo[4,3-b]pyridazin-3-yl)-2-methylpropionitrile was added, followed by refluxing under heating for 5 hours. After cooling, saline was added; the reaction mixture was extracted with ethyl acetate, washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; in 7.90 g of the residue was dissolved in 5 ml of pyridine; 5 ml of acetic anhydride was added, followed by stirring at room temperature for 15 hours. After saline was added, the reaction mixture was extracted with ethyl acetate, washed with saturated saline, and dried over magnesium sulfate. After concentration under reduced pressure, the residue was subjected to silica gel column chromatography and extracted with ethyl acetate-methanol-triethylamine (50:5:1). The desired fraction was collected and concentrated under reduced pressure; the residue (6.26 g) was dissolved in ethanol; 1.52 ml of a 4 N solution of hydrogen chloride in ethyl acetate was added, followed by concentration under reduced pressure. The residue was crystallized from methanol-ethanol (1:5), washed with ethanol-ethyl acetate (1:5), and dried, to yield 5.19 g of the title compound.

Melting point: 205–207° C.; Elemental analysis (for $C_{30}H_{35}N_6O_2Cl.0.5H_2O$): Calculated (%): C, 64.80; H, 6.52; N, 15.11; Found (%): C, 65.02; H, 6.28; N, 15.13.

EXAMPLE 17a

Production of Ethyl 2-[6-[3-[4-(Diphenylmethoxy) piperidino]propoxy][1,2,4]triazolo[4,3-b]pyridazin-3-yl]-2-methylpropionate fumarate 5.01 g of 2-[6-[3-[4-(diphenylmethoxy)piperidino] propoxy][1,2,4]triazolo[4,3-b]pyridazin-3-yl]-2-methylpropionitrile was dissolved in 20 ml of ethanol; 20 ml of a 2 N aqueous solution of sodium hydroxide was added, followed by refluxing under heating for 8 hours. After cooling, the ethanol was distilled off; 2 N hydrochloric acid was added to reach pH 5; sodium chloride was added; the reaction mixture was extracted with tetrahydrofuran and dried over magnesium sulfate. After concentration under reduced pressure, 2.18 g of the carboxylic acid obtained was dissolved in 20 ml of N,N-dimethylformamide; 0.85 ml of N-ethyldiisopropylamine was added. After stirring at room temperature for 5 minutes, 0.40 ml of iodoethane was added, followed by stirring at room temperature for 5 hours. After saline was added, the reaction mixture was extracted with ethyl acetate-tetrahydrofuran (1:1) and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 750 mg of the residue was dissolved in ethanol; a solution of 156 mg of fumaric acid in ethanol was added, followed by concentration under reduced pressure. The residue was crystallized from ethyl acetate-hexane (1:1), washed with diethyl ether-hexane (1:1), and dried, to yield 648 mg of the title compound.

Melting point: 173–175° C.; Elemental analysis (for $C_{36}H_{43}N_5O_8.H_2O$): Calculated (%): C, 62.50; H, 6.56; N, 10.12; Found (%): C, 62.24; H, 6.25; N, 9.78.

EXAMPLE 18a

Production of 2-[6-[3-[4-(Diphenylmethoxy) piperidino]propylamino][1,2,4]triazolo[4,3-b] pyridazin-3-yl]-2-methylpropionitrile fumarate 5.57 g of 4-(diphenylmethoxy)-1-piperidinepropanamine and 3.62 g of 2-[6-chloro[1,2,4]triazolo[4,3-b]pyridazin-3-yl]-2-methylpropionitrile were dissolved in 60 ml of 1-butanol; 5.65 ml of N-ethyldiisopropylamine was added, followed by refluxing under heating for 3.5 hours. After cooling, ethyl acetate was added; the reaction mixture was washed with saturated aqueous sodium bicarbonate, washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 7.18 g of the residue was dissolved in ethanol; a solution of 1.59 g of fumaric acid in ethanol was added, followed by concentration under reduced pressure. The residue was powdered from diethyl ether and dried to yield 7.71 g of the title compound.
Amorphous Elemental analysis (for $C_{34}H_{39}N_7O_5.0.5H_2O.0.5Et_2O$): Calculated (%): C, 64.36; H, 6.75; N, 14.60; Found (%): C, 64.00; H, 6.69; N, 14.65.

EXAMPLE 19a

Production of 2-[6-[3-[4-(Diphenylmethoxy) piperidino]propylamino][1,2,4]triazolo[4,3-b] pyridazin-3-yl]-2-methylpropionic Acid 6.16 g of 2-[6-[3-[4-(diphenylmethoxy)piperidino] propylamino][1,2,4]triazolo[4,3-b]pyridazin-3-yl]-2-methylpropionitrile was dissolved in 30 ml of ethanol; 30 ml of a 2 N aqueous solution of sodium hydroxide was added, followed by refluxing under heating for 1.5 days. After cooling, the ethanol was distilled off; the residue was washed with ethyl acetate; 1 N hydrochloric acid was added to reach pH 5; sodium chloride was added; the reaction mixture was extracted with tetrahydrofuran and dried over magnesium sulfate. After concentration under reduced pressure, the residue was powdered from ethyl acetate-diethyl ether (1:1); the powder was collected by filtration, washed with ethyl acetate-diethyl ether (1:1), and dried, to yield 1.04 g of the title compound.

$^1$H-NMR (DMSO-$d_6$-CDCl$_3$ (3:1)) δ ppm: 1.59 (6H, s), 1.50–2.05 (6H, m), 2.40–2.65 (5H, m), 2.91 (2H, br), 3.19 (2H, br), 5.61 (1H, s), 6.69 (1H, d, J=10.0 Hz), 7.18–7.42 (10H, m), 7.76 (1H, d, J=10.0 Hz). Melting point: 155–157° C.; Elemental analysis (for $C_{30}H_{36}N_6O_3.H_2O$): Calculated (%): C, 65.91; H, 7.01; N, 15.37; Found (%): C, 66.28; H, 7.16; N, 14.88.

EXAMPLE 20a

Production of Ethyl 2-[6-[3-[4-(Diphenylmethoxy) piperidino]propylamino][1,2,4]triazolo[4,3-b] pyridazin-3-yl]-2-methylpropionate fumarate 4.98 g of 2-[6-[3-[4-(diphenylmethoxy)piperidino] propylamino][1,2,4]triazolo[4,3-b]pyridazin-3-yl]-2-methylpropionic acid was dissolved in 50 ml of N,N-dimethylformamide; 1.95 ml of N-ethyldiisopropylamine was added. After stirring at room temperature for 10 minutes, 0.90 ml of iodoethane was added, followed by stirring at room temperature for 8.5 hours; 0.90 ml of iodoethane and 1.95 ml of N-ethyldiisopropylamine were added, followed by stirring at room temperature for 17 hours. After ice water was added, the reaction mixture was extracted with ethyl acetate-tetrahydrofuran (1:1) and dried over magnesium sulfate. After concentration under reduced pressure, the residue was subjected to silica gel column chromatography and eluted with ethyl acetate-methanoltriethylamine (50:5:1). The desired fraction was collected and concentrated under reduced pressure; 531 mg of the residue was dissolved in ethanol; a solution of 111 mg of fumaric acid in ethanol was added, followed by concentration under reduced pressure. The residue was powdered from diethyl ether; the powder was collected by filtration and dried to yield 563 mg of the title compound.

Melting point: 97–99° C.; Elemental analysis (for $C_{36}H_{44}N_6O_7 \cdot H_2O$): Calculated (%): C, 62.59; H, 6.71; N, 12.17; Found (%): C, 62.70; H, 6.90; N, 11.97.

EXAMPLE 21a

Production of Ethyl 6-[3-[4-(Diphenylmethoxy) piperidino]propylamino][1,2,4]triazolo[4,3-b] pyridazine-3-carboxylate 5.15 g of 4-(diphenylmethoxy)-1-piperidinepropanamine and 3.6 g of ethyl 6-chloro[1,2,4]triazolo[4,3-b]pyridazine-3-carboxylate were dissolved in 70 ml of N,N-dimethylformamide; 5.48 ml of N-ethyldiisdpropylamine was added, followed by stirring under heating at an external temperature of 70° C. for 4 hours. After cooling, cold saline was added; the reaction mixture was extracted with tetrahydrofuran and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; half of the precipitated crystal was recrystallized from ethanol-ethyl acetate (1:1), collected by filtration, and dried, to yield 2.13 g of the title compound.

Melting point: 129–133° C.; Elemental analysis (for $C_{29}H_{34}N_6O_3 \cdot 0.3H_2O$): Calculated (%): C, 66.98; H, 6.71; N, 16.16; Found (%): C, 67.09; H, 6.88; N, 16.02.

EXAMPLE 22a

Production of 6-[3-[4-(Diphenylmethoxy) piperidino]propylamino][1,2,4]triazolo[4,3-b] pyridazine-3-carboxylic Acid 1.31 g of ethyl 6-[3-[4-(diphenylmethoxy)piperidino] propylamino][1,2,4]triazolo[4,3-b]pyridazine-3-carboxylate was dissolved in 8 ml of ethanol; 8 ml of a 1 N aqueous solution of sodium hydroxide was added, followed by refluxing under heating for 3 hours. After cooling, the ethanol was distilled off; the residue was washed with ethyl acetate; 1 N hydrochloric acid was added to reach pH 5. The precipitated crystal was collected by filtration, washed with water and ethyl acetate, and dried, to yield 1.19 g of the title compound.

Melting point: 102–104° C.; Elemental analysis (for $C_{27}H_{30}N_6O_3 \cdot 2H_2O$): Calculated (%): C, 62.05; H, 6.56; N, 16.00; Found (%): C, 61.82; H, 6.40; N, 16.06.

EXAMPLE 23a

Production of 2-[6-[3-[4-(Diphenylmethoxy) piperidino]propoxy][1,2,4]triazolo[4,3-b]pyridazin-3-yl]-2-methylpropionamide 409 mg of 2-[6-[3-[4-(diphenylmethoxy)piperidino] propoxy][1,2,4]triazolo[4,3-b]pyridazin-3-yl]-2-methylpropionitrile was dissolved in 6 ml of 2-propanol; 3.5 ml of a 1 N aqueous solution of sodium hydroxide was added, followed by stirring under heating at an external temperature of 40° C. for 12 hours. After cooling, the 2-propanol was distilled off; the residue was extracted with ethyl acetate-tetrahydrofuran (1:1), washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the residue was crystallized from ethyl acetate-diethyl ether (1:1), washed with diethyl ether, and dried, to yield 293 mg of the title compound.

Melting point: 133–136° C.; Elemental analysis (for $C_{30}H_{36}N_6O_3 \cdot 0.5H_2O$): Calculated (%): C, 67.02; H, 6.94; N, 16.63; Found (%): C, 67.17; H, 6.84; N, 16.35.

EXAMPLE 24a

Production of 2-[6-[3-[4-(Diphenylmethoxy) piperidino]propylamino][1,2,4]triazolo[4,3-b] pyridazin-3-yl]-2-methylpropionamide Hydrochloride 644 mg of 2-[6-[3-[4-(diphenylmethoxy)piperidino] propylamino][1,2,4]triazolo[4,3-b]pyridazin-,3-yl]-2-methylpropionic acid was dissolved in 6 ml of N,N-dimethylformamide; under ice cooling, 474 mg of N,N'-carbonyldiimidazole was added. After stirring at room temperature for 4 hours, 134 mg of ammonium chloride was added under ice cooling, followed by stirring at room temperature for 2 hours. After ice water was added, the reaction mixture was extracted with ethyl acetate-tetrahydrofuran (1:1), washed with saturated saline, and dried over magnesium sulfate. After concentration under reduced pressure, the residue was subjected to silica gel column chromatography and eluted with ethyl acetate. The desired fraction was collected and concentrated under reduced pressure; the residue was dissolved in ethanol; 0.30 ml of a 4 N solution of hydrogen chloride in ethyl acetate was added, followed by concentration under reduced pressure. The residue was crystallized from ethanol-acetone (1:5) and dried to yield 301 mg of the title compound.

Melting point: 226–227° C.; Elemental analysis (for $C_{30}H_{38}N_7O_2Cl \cdot 0.3H_2O$): Calculated (%): C, 63.26; H, 6.83; N, 17.21; Found (%): C, 63.27; H, 6.68; N, 17.11.

EXAMPLE 25a

Production of N-[6-[3-[4-(Diphenylmethoxy) piperidino]propylamino][1,2,4]triazolo[4,3-b] pyridazine-3-carbonyl]-2,2-dimethylglycine Ethyl Ester 1.25 g of 4-(diphenylmethoxy)-1-piperidinepropanamine and 1.20 g of N-(6-chloro[1,2,4]triazolo[4,3-b]pyridazine-3-carbonyl)-2,2-dimethylglycine ethyl ester were dissolved in 20 ml of N,N-dimethylformamide; 1.33 ml of N-ethyldiisopropylamine was added, followed by stirring under heating at an external temperature of 60° C. for 7.5 hours. After cooling, cold aqueous sodium bicarbonate was added; the reaction mixture was extracted with ethyl acetate, washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; the precipitated crystal was recrystallized from ethanol-ethyl acetate fir (1:3), collected by filtration, and dried, to yield 1.17 g of the title compound.

Melting point: 165–167° C.; Elemental analysis (for $C_{33}H_{41}N_7O_4$): Calculated (%): C, 66.09; H, 6.89; N, 16.35; Found (%): C, 65.91; H, 6.76; N, 16.44.

EXAMPLE 26a

Production of N-[6-[3-[4-(Diphenylmethoxy)piperidino]propylamino][1,2,4]triazolo[4,3-b]pyridazine-3-carbonyl]-2,2-dimethylglycine 830 mg of N-[6-[3-[4-(diphenylmethoxy)piperidino]propylamino][1,2,4]triazolo[4,3-b]pyridazine-3-carbonyl]-2,2-dimethylglycine ethyl ester was dissolved in 10 ml of ethanol; 3.2 ml of a 1 N aqueous solution of sodium hydroxide was added, followed by stirring at room temperature for 17 hours. After the ethanol was distilled off, 1 N hydrochloric acid was added to reach pH 4.5. The precipitated crystal was collected by filtration, washed with water and ethanol, and dried, to yield 610 mg of the title compound.

Melting point: 191–193° C.; Elemental analysis (for $C_{31}H_{37}N_7O_4 \cdot 1.5H_2O$): Calculated (%): C, 62.19; H, 6.73; N, 16.38; Found (%): C, 62.48; H, 6.72; N, 16.53.

EXAMPLE 27a

Production of N-[6-[3-[4-(Diphenylmethoxy)piperidino]propoxy][1,2,4]triazolo[4,3-b]pyridazine-3-carbonyl]-2,2-dimethylglycine ethyl ester difumarate 1.04 g of 4-(diphenylmethoxy)-1-piperidinepropanol was dissolved in 14 ml of N,N-dimethylformamide; 141 mg of sodium hydride (60% in oil) was added, followed by stirring at room temperature under reduced pressure for 50 minutes. Under ice cooling, 1.00 g of N-(6-chloro[1,2,4]triazolo[4,3-b]pyridazine-3-carbonyl)-2,2-dimethylglycine ethyl ester was added, followed by stirring at ice temperature for 1 hour, then at room temperature for 2 hours. After saline was added, the reaction mixture was extracted with ethyl acetate-tetrahydrofuran (1:1) and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 1.62 g of the residue was dissolved in 2 ml of pyridine; 1 ml of acetic anhydride was added, followed by stirring at room temperature for 15 hours. After saline was added, the reaction mixture was extracted with ethyl acetate, washed with saturated saline, and dried over magnesium sulfate. After concentration under reduced pressure, the residue was subjected to silica gel column chromatography and eluted with ethyl acetate-methanol-triethylamine (50:5:1). The desired fraction was collected and concentrated under reduced pressure; 1.32 g of the residue was dissolved in ethanol; a solution of 511 mg of fumaric acid in ethanol was added, followed by concentration under reduced pressure. The residue was powdered from diethyl ether and dried to yield 1.53 g of the title compound.
Amorphous Elemental analysis (for $C_{41}H_{48}N_6O_{13}$): Calculated (%): C, 59.13; H, 5.81; N, 10.09; Found (%): C, 59.15; H, 5.97; N, 10.16.

EXAMPLE 28a

Production of N-[6-[3-[4-(Diphenylmethoxy)piperidino]propoxy][1,2,4]triazolo[4,3-b]pyridazine-3-carbonyl]-2,2-dimethylglycine 690 mg of N-[6-[3-[4-(diphenylmethoxy)piperidino]propoxy][1,2,4]triazolo[4,3-b]pyridazine-3-carbonyl]-2,2-dimethylglycine ethyl ester was dissolved in 8 ml of tetrahydrofuran; 1.3 ml of a 1 N aqueous solution of sodium hydroxide was added, followed by stirring at room temperature for 19 hours. The tetrahydrofuran was distilled off; 1 N hydrochloric acid was added to reach pH 5. Saturated saline was added; the reaction mixture was extracted with tetrahydrofuran and dried over magnesium sulfate. After concentration under reduced pressure, the precipitated crystal was washed with ethyl acetate and dried to yield 459 mg of the title compound.

Melting point: 163–165° C.; Elemental analysis (for $C_{31}H_{36}N_6O_5 \cdot 3H_2O$): Calculated (%): C, 59.41; H, 6.75; N, 13.41; Found (%): C, 59.04; H, 6.39; N, 13.27.

EXAMPLE 29a

Production of N-[6-[3-[4-(Diphenylmethoxy)piperidino]propylamino][1,2,4]triazolo[4,3-b]pyridazine-3-carbonyl]glycine ethyl ester 1.58 g of 4-(diphenylmethoxy)-1-piperidinepropanamine and 1.38 g of N-(6-chloro[1,2,4]triazolo[4,3-b]pyridazine-3-carbonyl)glycine ethyl ester were dissolved in 15 ml of N,N-dimethylformamide; 1.68 ml of N-ethyldiisopropylamine was added, followed by stirring under heating at an external temperature of 70° C. for 5 hours. After cooling, water was added; the reaction mixture was extracted with tetrahydrofuran. After concentration under reduced pressure, the precipitated crystal was twice recrystallized from ethanol-tetrahydrofuran (1:1), collected by filtration, and dried, to yield 995 mg of the title compound.

Melting point: 152–155° C.; Elemental analysis (for $C_{31}H_{37}N_7O_4 \cdot 0.5H_2O$): Calculated (%): C, 64.12; H, 6.60; N, 16.88; Found (%): C, 64.10; H, 6.55; N, 16.87.

EXAMPLE 30a

Production of N-[6-[3-[4-(Diphenylmethoxy)piperidino]propylamino][1,2,4]triazolo[4,3-b]pyridazine-3-carbonyl]glycine 1.29 g of N-[6-(3-[4-(diphenylmethoxy)piperidino]propylamino)[1,2,4]triazolo[4,3-b]pyridazine-3-carbonyl]glycine ethyl ester was dissolved in 10 ml of ethanol; 4.5 ml of a 1 N aqueous solution of sodium hydroxide was added, followed by stirring at room temperature for 30 minutes. The ethanol was distilled off under reduced pressure; the reaction mixture was adjusted to pH 4.5 using 1 N hydrochloric acid. The precipitated crystal was collected by filtration, washed with water and acetone, and dried, to yield 831 mg of the title compound.

Melting point: 182–184° C.; Elemental analysis (for $C_{29}H_{33}N_7O_4 \cdot H_2O$): Calculated (%): C, 62.02; H, 6.28; N, 17.46; Found (%): C, 62.32; H, 6.10; N, 17.46.

PREPARATION EXAMPLE 1a (1) Compound of Example 22a 10.0 mg
(2) Lactose 60.0 mg
(3) Corn starch 35.0 mg
(4) Gelatin 3.0 mg
(5) Magnesium stearate 2.0 mg A mixture of 10.0 mg of the compound obtained in Example 22a, 60.0 mg of lactose and 35.0 mg of corn starch was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

PREPARATION EXAMPLE 2a (1) Compound of Example 22a 10.0 mg (2) Lactose 70.0 mg (3) Corn starch 50.0 mg (4) Soluble starch 7.0 mg (5) Magnesium stearate 3.0 mg After 10.0 mg of the compound obtained in Example 22a and 3.0 mg of magnesium stearate were granulated using 0.07 ml of an aqueous solution of soluble starch (containing 7.0 mg of soluble starch), the resulting granules were dried and mixed with 70.0 mg of lactose and 50.0 mg of corn starch. The mixture was compressed to yield tablets.

PREPARATION EXAMPLE 3a (1) Compound of Example 22a 5.0 mg (2) Sodium chloride 20.0 mg (3) Distilled water was added to reach a total volume of 2 ml.

5.0 mg of the compound obtained in Example 22a and 20.0 mg of sodium chloride were dissolved in distilled water and diluted with water to reach a total volume of 2.0 ml. The resulting solution was filtered and aseptically packed in a 2 ml ampule. After sterilization, the ampule was sealed to yield a solution for injection.

EXPERIMENTAL EXAMPLE 1a

Effect on Histamine-induced Skin Reactions in Guinea Pigs

Male Hartley guinea pigs weighing about 500 g were used. After the dorsal hair was shaved under ether anesthesia, 1 ml of a 2.5% pontamine sky blue solution was injected intravenously administered, and then 0.1 ml of histamine at 3 $\mu$g/ml was injected intradermally into 2 sites (left and right) in the back. Thirty minutes after the injection of histamine, the animals were killed by bleeding and the skin was removed. Two perpendicular diameters (mm) of each blue spot on the inside of the skin were measured and multiplied; the mean for the two products was taken as the microvascular permeability index. Test compounds were suspended in a 5% gum arabic solution and orally administered in a volume of 0.2 ml/100 g body weight 1 hour before histamine administration. Animals in the control group received the same volume of a 5% gum arabic solution. The suppression rate of the sample for the title reaction was calculated using Equation 1, and the results are given in Table 1.

Inhibition (%) of histamine-induced skin reactions=100×(1−vascular permeability index in the presence of drug/vascular permeability index in control group)   Equation 1

TABLE 1

Effects of Test Compounds on Histamine-induced Skin Vascular Permeability

| Compound | Suppression (%) of histamine-induced skin vascular permeability elevation, oral administration at 3 mg/kg |
|---|---|
| Example 7a | 89 |
| Example 10a | 91 |
| Example 13a | 79 |
| Example 22a | 86 |

EXPERIMENTAL EXAMPLE 2a

1) Preparation of Guinea Pig Eosinophils

To male Hartley guinea pigs, 2 ml of equine serum (Bio-Whittaker, Inc.) was intraperitoneally administered once weekly for 8 consecutive weeks. At 48 hours after final administration, 75 ml of physiological saline was intraperitoneally injected, after which the saline was recovered and centrifuged at 400×g for 5 minutes. The resulting sediment was suspended in 5 ml of Percoll solution (density (d)=1.07) and layered on top of the multiple layers of different densities of Percoll solution (density(d)=1.112, 5 ml; d=1.095, 10 ml; d=1.090, 10 ml; d=1.085, 5 ml), followed by centrifugation at 1,000×g for 25 minutes (20° C.). The cell layer formed at the interface between densities 1.112 and 1.095 was collected. Erythrocytes present in the collected cell sediment were removed by hypotonic treatment (suspended in water for 30 minutes).

The cell sediment was washed 3 times with Hanks' solution containing 10 mM Hepes (Dojin Kagaku) (Hanks-Hepes) and suspended in a Hanks-Hepes solution containing 2% human serum albumin (Wako Pure Chemical Industry or Sigma) (Hanks-Hepes-HSA) to a final concentration of 5.56×10$^6$ cells/ml. Eosinophil purity was 90%, viability being over 98%.

2) Determination of Chemotactic Reaction Suppression

To a 24-well petri dish, which serves as a lower chamber, 600 $\mu$l of Hanks-Hepes-HSA solution containing LTB$_4$ (final concentration 10$^{-8}$ M, Cascade Biochemical Ltd.), was transferred, followed by incubation at 37° C. for 30 minutes in a carbon dioxide incubator. Separately, 200 $\mu$l of eosinophil suspension (5×10$^6$ cells/ml), previously incubated at 37 C for 15 minutes, was added to Chemotaxicell (polycarbonate membrane, pore size 3 $\mu$m, thickness 10 $\mu$m), which serves as an upper chamber, after the upper chamber was attached to the 24-well petri dish. After 2 hours of reaction in the CO$_2$ incubator, the Chemotaxicell was removed; 60 $\mu$l of a 2% (w/v) solution of EDTA in physiological saline was added to the liquid in the lower chamber. After the mixture was on cooled ice, the cells migrating into the lower chamber were counted using a blood cell counter [Coulter Counter (trade name)]. The test drug, dissolved in N,N-dimethyl formamide (DMF), was added to both the upper and lower chambers to a final concentration of 10–5 M.

Chemotactic reaction suppression rate=[1−(number of migrating cells in the presence of drug/number of migrating cells in the absence of drug).]×100   Equation 2

Suppression rates of LTB$_4$-induced chemotactic reaction by test substances (1×10$^{-5}$ M) were calculated using the above equation. The results are shown in Table 2.

TABLE 2

Action on $LTB_4$-induced Chemotactic Reaction
in Guinea Pig Eosinophils

| Compound | Suppression rate (%) |
| --- | --- |
| Example 7a | 36 |
| Example 10a | 60 |
| Example 13a | 41 |
| Example 22a | 50 |

COMPOUND (Ib):

REFERENCE EXAMPLE 1b

Production of 4-(Diphenylmethoxy)-1-piperidinepropanol 2.67 g of 4-diphenylmethoxypiperidine was dissolved in 20 ml of N,N-dimethylformamide; 1.09 ml of 3-bromopropanol and 1.66 g of potassium carbonate were added, followed by stirring at room temperature for 40 hours. After ice water was poured, the reaction mixture was extracted with ethyl acetate; the extract was washed with saline and dried over magnesium sulfate. After concentration under reduced pressure, the residue was subjected to silica gel column chromatography and eluted with ethyl acetate-methanol-triethylamine (90:10:1). The desired fraction was collected and concentrated to yield 2.32 g of the title compound.

$^1$H-NMR (CDCl$_3$) δ ppm: 1.60–1.95 (6H, m), 2.10–2.35 (2H, m), 2.58 (2H, t, J=5 Hz), 2.75–2.90 (2H, m), 3.3–3.6 (1H, m), 3.78 (2H, t, J=5 Hz), 5.50 (1H, s), 7.1–7.5 (10H, m).

REFERENCE EXAMPLE 2b

Production of 6-Chloro-2-methyl[1,2,4]triazolo[4,3-b]pyridazin-3(2H)-one 0.853 g of 6-chloro[1,2,4]triazolo[4,3-b]pyridazin-3(2H)-one was dissolved in 5 ml of N,N-dimethylformamide; 0.83 g of potassium carbonate was added; with stirring at room temperature, 0.5 ml of methyl iodide was added. After stirring at room temperature for 15 hours, ice water and saline were added; the reaction mixture was extracted with ethyl acetate-tetrahydrofuran (1:1); the extract was washed with saline and dried over magnesium sulfate. After concentration under reduced pressure, the crystal obtained was collected by filtration, washed with diethyl ether, and dried, to yield 0.62 g of the title compound.

Melting point: 176–177° C.; Elemental analysis (for C$_6$H$_5$N$_4$OCl): Calculated (%): C, 39.04; H, 2.73; N, 30.75; Found (%): C, 38.98; H, 2.67; N, 30.75.

REFERENCE EXAMPLE 3b

Production of 6-Chloro-2-triphenylmethyl[1,2,4]triazolo[4,3-b]pyridazin-3(2H)-one 0.341 g of 6-chloro[1,2,4]triazolo[4,3-b]pyridazin-3(2H)-one and 0.669 g of chlorotriphenylmethane were dissolved in 5 ml of N,N-dimethylformamide; 0.414 ml of N-ethyldiisopropylamine was added, followed by stirring at room temperature for 2 days. After water was added, the reaction mixture was extracted with ethyl acetate; the extract was washed with saline and dried over magnesium sulfate. After concentration under reduced pressure, the residue was subjected to silica gel column chromatography and eluted with hexane-ethyl acetate (2:1). The desired fraction was collected and concentrated; the crystal obtained was collected by filtration, washed with diethyl ether, and dried, to yield 0.591 g of the title compound.

Melting point: 246–247° C.; Elemental analysis (for C$_{24}$H$_{17}$N$_4$OCl): Calculated (%): C, 69.82; H, 4.15; N, 13.57; Found (%): C, 69.31; H, 4.33; N, 13.07.

EXAMPLE 1b

Production of 6-[3-[4-(Diphenylmethoxy)piperidino]propylamino]-2-methyl[1,2,4]triazolo[4,3-b]pyridazin-3(2H)-one 0.277 g of 6-chloro-2-methyl[1,2,4]triazolo[4,3-b]pyridazin-3(2H)-one was dissolved in 2 ml of N,N-dimethylformamide; 0.487 g of 4-(diphenylmethoxy)-1-piperidinepropanamine was added, followed by stirring in an oil bath (bath temperature 140–150° C.) for 1 hour. After cooling, ice water and an aqueous solution of sodium hydrogen carbonate were added; the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (90:10:1). The desired fraction was collected and concentrated; the crystal obtained was filtered, washed with diethyl ether, and dried, to yield 0.19 g of the title compound.

Melting point: 171–172° C.; Elemental analysis (for C$_{21}$H$_{32}$N$_6$O$_2$): Calculated (%): C, 68.62; H, 6.82; N, 17.78; Found (%): C, 68.51; H, 6.72;N, 17.75.

EXAMPLE 2b

Production of 6-[3-[4-(Diphenylmethoxy)piperidino]propoxy]-2-methyl[1,2,4]triazolo[4,3-b]pyridazin-3(2H)-one 0.52 g of 4-(diphenylmethoxy)-1-piperidinepropanol was dissolved in 3 ml of N,N-dimethylformamide; 0.0704 g of 60% oily sodium hydride was added, followed by stirring at room temperature for 1 hour. 0.325 g of 6-chloro-2-methyl[1,2,4]triazolo[4,3-b]pyridazin-3(2H)-one was added, followed by stirring at room temperature for 2 hours. After ice water was added, the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (90:10:1). The desired fraction was collected and concentrated; the crystal obtained was filtered, washed with diethyl ether, and dried, to yield 0.502 g of the title compound.

Melting point: 139–140° C.; Elemental analysis (for C$_{27}$H$_{31}$N$_5$O$_3$): Calculated (%): C, 68.48; H, 6.60; N, 14.79; Found (%): C, 68.32; H, 6.59; N, 14.58.

EXAMPLE 3b

Production of 6-[3-[4-(Diphenylmethoxy)piperidino]propylamino][1,2,4]triazolo[4,3-b]pyridazin-3(2H)-one 0.512 g of 6-chloro[1,2,4]triazolo[4,3-b]pyridazin-3(2H)-one was dissolved in 15 ml of n-butanol; 0.88 g of 4-(diphenylmethoxy)-1-piperidinepropanamine and 1.04 ml of N-ethyldiisopropylamine were added, followed by refluxing under heating in an oil bath for 5 hours. After cooling, the n-butanol was mostly distilled off under reduced pressure; to the residue, an aqueous solution of sodium hydrogen carbonate was added; the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (85:15:1). The desired fraction was collected and concentrated; the crystal obtained was filtered, washed with diethyl ether, and dried, to yield 0.35 g of the title compound.

Melting point: 156–170° C.; Elemental analysis (for $C_{26}H_{30}N_6O_2 \cdot 2H_2O$): Calculated (%): C, 65.52; H, 6.72; N, 17.64; Found (%): C, 65.78; H, 6.71; N, 17.52.

EXAMPLE 4b

Production of 6-[3-[4-(Diphenylmethoxy) piperidino]propoxy][1,2,4]triazolo[4,3-b]pyridazin-3 (2H)-one 0.326 g of 4-(diphenylmethoxy)-1-piperidinepropanol was dissolved in 3 ml of N,N-dimethylformamide; 0.044 g of 60% oily sodium hydride was added, followed by stirring at room temperature for 1 hour. 0.326 g of 6-chloro-2-triphenylmethyl[1,2,4]triazolo[4,3-b]pyridazin-3(2H)-one was added, followed by stirring at room temperature for 14 hours. After ice water was added, the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol (95:5). The desired fraction was collected and concentrated to yield 0.58 g of 6-[3-[4-(diphenylmethoxy)piperidino]propoxy]-2-triphenylmethyl [1,2,4]triazolo[4,3-b]pyridazin-3(2H)-one as an oily substance. 0.58 g of the oily substance obtained was dissolved in 10 ml of acetone; 467 mg of p-toluenesulfonic acid hydrate was added, followed by refluxing under heating in an oil bath for 5 hours. After cooling, the acetone was mostly distilled off under reduced pressure; to the residue, an aqueous solution of sodium hydrogen carbonate was added; the reaction mixture was extracted with ethyl acetate-tetrahydrofuran (2:1); the extract was washed with saturated saline and dried over magnesium sulfate. After concentration under reduced pressure, the residue was subjected to silica gel column chromatography and eluted with ethyl acetate-methanol-triethylamine (85:15:1). The desired fraction was collected and concentrated; the crystal obtained was filtered, washed with ethyl acetate, and dried, to yield 0.137 g of the title compound.

Melting point: 209–211° C.; Elemental analysis (for $C_{26}H_{29}N_5O_3$): Calculated (%): C, 67.96; H, 6.36; N, 15.24; Found (%): C, 67.72; H, 6.16; N, 15.09.

EXAMPLE 5b

Production of Ethyl 2-[6-[3-[4-(Diphenylmethoxy) piperidino]propoxy]-3-oxo[1,2,4]triazolo[4,3-b] pyridazin-2(3H)-yl]acetate 0.459 g of 6-(3-[4-(diphenylmethoxy)piperidino] propoxy][1,2,4]triazolo[4,3-b]pyridazin-3(2H)-one was suspended in 6 ml of N,N-dimethylformamide; 0.048 g of 60% oily sodium hydride was added, followed by stirring at room temperature for 1 hour. Under ice cooling, 0.133 ml of ethyl bromoacetate was added, followed by stirring at room temperature for 4 hours. After ice water was added, the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (185:15:2). The desired fraction was collected and concentrated; the crystal obtained was filtered, washed with diethyl ether, and dried, to yield 0.235 g of the title compound.

Melting point: 124–125° C.; Elemental analysis (for $C_{30}H_{35}N_5O_5$): Calculated (%): C, 66.04; H, 6.47; N, 12.84; Found (%): C, 65.82; H, 6.40; N, 12.81.

EXAMPLE 6b

Production of Ethyl 2-[6-[3-[4-(Diphenylmethoxy) piperidino]propoxy]-3-oxo[1,2,4]triazolo[4,3-b] pyridazin-2(3H)-yl]-2-methylpropionate Hydrochloride 0.459 g of 6-[3-[4-(diphenylmethoxy)piperidino] propoxy][1,2,4]triazolo[4,3-b]pyridazin-3(2H)-one was suspended in 6 ml of N,N-dimethylformamide; 0.048 g of 60% oily sodium hydride was added, followed by stirring at room temperature for 30 minutes. 0.294 ml of ethyl 2-bromoisobutyrate was added, followed by stirring in an oil bath (bath temperature 110° C.) for 4 hours. After cooling, 0.048 g of 60% oily sodium hydride and 0.294 ml of ethyl 2-bromoisobutyrate were added, followed.by stirring in an oil bath (bath temperature 110° C.) for 10 hours. After cooling, ice water was added; the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (185:15:2). The desired fraction was collected and concentrated to yield 0.401 g of ethyl 2-[6-[3-[4-(diphenylmethoxy)piperidino] propoxy]-3-oxo[1,2,4]triazolo[4,3-b]pyridazin-2(3H)-yl]-2-methylpropionate as an oily substance. This oily substance was dissolved in 5 ml of ethyl acetate; 0.5 ml of a 4 N solution of hydrogen chloride in ethyl acetate was added, followed by concentration; the residue was powdered from diethyl ether; the powder was collected by filtration and dried to yield 0.300 g of the title compound.

Melting point: 129° C. (softened); Elemental analysis (for $C_{32}H_{39}N_5O_5 \cdot HCl \cdot H_2O$): Calculated (%): C, 61.19; H, 6.74; N, 11.15; Found (%): C, 61.37; H, 6.75; N, 11.21.

EXAMPLE 7b

Production of ethyl 2-[6-[3-[4-(Diphenylmethoxy) piperidino]propylamino]-3-oxo[1,2,4]triazolo[4,3-b] pyridazin-2(3H)-yl]acetate 0.550 g of 6-[3-[4-(diphenylmethoxy)piperidino] propylamino][1,2,4]triazolo[4,3-b]pyridazin-3(2H)-one was suspended in 3 ml of N,N-dimethylformamide; 0.058 g of 60% oily sodium hydride was added, followed by stirring at room temperature for 1 hour. Under ice cooling, 0.160 ml of ethyl bromoacetate was added, followed by stirring at room temperature for 2 hours. After ice water was added, the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (90:10:1). The desired fraction was collected and concentrated; the crystal obtained was filtered, washed with diethyl ether, and dried, to yield 0.332 g of the title compound.

Melting point: 137–139° C.; Elemental analysis (for $C_{30}H_{36}N_6O_4$): Calculated (%): C, 66.15; H, 6.66; N, 15.43; Found (%): C, 65.98; H, 6.54; N, 15.33.

EXAMPLE 8b

Production of Ethyl 2-[6-[3-[4-(Diphenylmethoxy) piperidino]propylamino]-3-oxo[1,2,4]triazolo[4,3-b] pyridazin-2(3H)-yl]-2-methylpropionate Hydrochloride 0.606 g of 6-[3-[4-(diphenylmethoxy)piperidino] propylamino][1,2,4]triazolo[4,3-b]pyridazin-3(2H)-one was suspended in 3 ml of N,N-dimethylformamide; 0.063 g of 60% oily sodium hydride was added,-followed by stirring at room temperature for 1 hour. 0.253 ml of ethyl 2-bromoisobutyrate was added, followed by stirring in an oil bath (bath temperature 80° C.) for 17 hours. After cooling, 0.063 g of 60% oily sodium hydride and 0.253 ml of ethyl 2-bromoisobutyrate were added, followed by stirring in an oil bath (bath temperature 80° C.) for 3 hours. After cooling, ice water was added; the reaction mixture was extracted with ethyl acetate; the extract was washed with saturated saline and dried over magnesium sulfate. After concentration under reduced pressure, the residue was subjected to silica gel column chromatography and eluted with ethyl acetate-methanol-triethylamine (90:10:1). The desired fraction was collected and concentrated to yield 0.38 g of ethyl 2-[6-[3-[4-(diphenylmethoxy)piperidino]propylamino]-3-oxo[1,2,4]triazolo[4,3-b]pyridazin-2(3H)-yl]-2-methylpropionate as an oily substance. This oily substance was dissolved in 5 ml of ethyl acetate; 0.5 ml of a 4 N solution of hydrogen chloride in ethyl acetate was added, followed by concentration; the residue was powdered from diethyl ether, collected by filtration, and dried, to yield 0.342 g of the title compound.

Melting point: 162° C.; Elemental analysis (for $C_{32}H_{40}N_6O_4 \cdot HCl \cdot (C_2H_5)_2O$): Calculated (%): C, 61.83; H, 7.35; N, 12.02; Found (%): C, 62.16; H, 7.02; N, 12.15.

EXAMPLE 9b

Production of 2-[6-[3-[4-(Diphenylmethoxy) piperidino]propylamino]-3-oxo[1,2,4]triazolo[4,3-b] pyridazin-2(3H)-yl]-2-methylpropionic Acid 0.50 g of ethyl 2-[6-[3-[4-(diphenylmethoxy)piperidino] propylamino]-3-oxo[1,2,4]triazolo[4,3-b]pyridazin-2(3H)-yl]-2-methylpropionate was dissolved in 3 ml of ethanol; 2.2 ml of a 1 N aqueous solution of sodium hydroxide was added, followed by stirring at room temperature for 24 hours. After the ethanol was distilled off under reduced pressure, the residue was diluted with water and washed with ethyl acetate. To the water layer, 2.2 ml of 1 N hydrochloric acid was added; the mixture was saturated with sodium chloride and extracted with ethyl acetate-tetrahydrofuran (2:1); the extract was washed with saturated saline and dried over magnesium sulfate. After concentration under reduced pressure, the residue was powdered by the addition of ethyl acetate, collected by filtration, washed with ethyl acetate, and dried, to yield 0.203 g of the title compound.

Melting point: 181–185° C.; Elemental analysis (for $C_{30}H_{36}N_6O_4 \cdot 2.5H_2O$): Calculated (%): C, 61.10; H, 7.01; N, 14.25; Found (%): C, 61.31; H, 7.02; N, 13.91.

EXAMPLE 10b

Production of 6-[3-[4-(Diphenylmethoxy) piperidino]propylamino]-2-(pivaloyloxymethyl)[1,2,4]triazolo[4,3-b]pyridazin-3(2H)-one 0.560 g of 6-[3-[4-(diphenylmethoxy)piperidino] propylamino][1,2,4]triazolo[4,3-b]pyridazin-3(2H)-one was suspended in 3 ml of N,N-dimethylformamide; 0.210 g of potassium carbonate and 0.220 ml of chloromethyl pivalate were added, followed by stirring at room temperature for 15 hours. After ice water was added, the reaction mixture was extracted with ethyl acetate; the extract was washed with saline and dried over magnesium sulfate. After concentration under reduced pressure, the residue was subjected to silica gel column chromatography and eluted with ethyl acetate-methanol-triethylamine (185:15:2). The desired fraction was collected and concentrated; the crystal obtained was filtered, washed with diethyl ether, and dried, to yield 0.39 g of the title compound.

Melting point: 168–171° C.; Elemental analysis (for $C_{32}H_{40}N_6O_4$): Calculated (%): C, 67.11; H, 7.04; N, 14.67; Found (%): C, 67.01; H, 6.79; N, 14.75.

EXAMPLE 11b

Production of pivaloyloxymethyl 2-[6-[3-[4-(Diphenylmethoxy)piperidino]propylamino]-3-oxo [1,2,4]triazolo[4,3-b]pyridazin-2(3H)-yl]-2-methylpropionate 0.750 g of ethyl 2-[6-[3-[4-(diphenylmethoxy)piperidino] propylamino]-3-oxo[1,2,4]triazolo[4,3-b]pyridazin-2(3H)-yl]-2-methylpropionate was dissolved in 5 ml of ethanol; 3.28 ml of a 1 N aqueous solution of sodium hydroxide was added, followed by stirring at room temperature for 24 hours. After the ethanol was distilled off under reduced pressure, the residue was diluted with water and washed with ethyl acetate; to the water layer, 3.28 ml of 1 N hydrochloric acid was added; the reaction mixture was extracted with ethyl acetate-tetrahydrofuran (1:1); the extract was washed with saturated saline and dried over magnesium sulfate. After concentration under reduced pressure, the residue was dissolved in 5 ml of N,N-dimethylformamide; 0.273 g of potassium carbonate and 0.285 ml of chloromethyl pivalate were added, followed by stirring at room temperature for 15 hours. After ice water was added, the reaction mixture was extracted with ethyl acetate; the extract was washed with saline and dried over magnesium sulfate. After concentration under reduced pressure, the residue was subjected to silica gel column chromatography and eluted with ethyl acetate-methanol-triethylamine (185:15:2). The desired fraction was collected and concentrated; the residue was crystallized from diethyl ether, collected by filtration, and dried, to yield 0.524 g of the title compound.

Melting point: 162° C.; Elemental analysis (for $C_{36}H_{46}N_6O_6$): Calculated (%): C, 65.63; H, 7.04; N, 12.76; Found (%): C, 65.52; H, 6.80; N, 12.86.

EXAMPLE 12b

Production of pivaloyloxymethyl 2-[6-[3-[4-(Diphenylmethoxy)piperidino]propoxy]-3-oxo[1,2,4] triazolo[4,3-b]pyridazin-2(3H)-yl]-2-methylpropionate Fumarate 0.750 g of ethyl 2-[6-[3-[4-(diphenylmethoxy)piperidino] propoxy]-3-oxo[1,2,4]triazolo[4,3-b]pyridazin-2(3H)-yl]-2-methylpropionate was dissolved in 6 ml of ethanol; 3.9 ml of a 1 N aqueous solution of sodium hydroxide was added, followed by stirring at room temperature for 40 hours. After the ethanol was distilled off under reduced pressure, the residue was diluted with water and washed with ethyl acetate; to the water layer, 3.9 ml of 1 N hydrochloric acid was added; the reaction mixture was extracted with ethyl acetate-tetrahydrofuran (1:1); the extract was washed with saturated saline and dried over magnesium sulfate. After concentration under reduced pressure, the residue was dissolved in 5 ml of N,N-dimethylformamide; 0.324 g of potassium carbonate and 0.339 ml of chloromethyl pivalate were added, followed by stirring at room temperature for 18 hours. After ice water was added, the reaction mixture was extracted with ethyl: acetate; the extract was washed with saline and dried over magnesium sulfate. After concentration under reduced pressure, the residue was subjected to silica gel column chromatography and eluted with ethyl acetate-methanol (95:5). The desired fraction was collected and concentrated to yield 0.50 g of pivaloyloxymethyl 2-[6-[3-[4-(diphenylmethoxy)piperidino]propoxy]-3-oxo[1,2,4]triazolo[4,3-b]pyridazin-2(3H)-yl]-2-methylpropionate as an oily substance. 0.50 g of this oily substance was dissolved in 5 ml of ethyl acetate; a solution of 87 mg of fumaric acid in 3 ml of methanol was added, followed by concentration under reduced pressure. The residue was crystallized from ethyl acetate, collected by filtration, and dried to yield 15 0.463 g of the title compound.

Melting point: 160–162° C.; Elemental analysis (for $C_{40}H_{49}N_5O_{11} \cdot 0.5H_2O$): Calculated (%): C, 61.21; H, 6.42; N, 8.92; Found (%): C, 61.37; H, 6.50; N, 8.88.

EXAMPLE 13b

Production of 6-[3-[4-(Diphenylmethoxy) piperidino]propoxy]-2-(pivaloyloxymethyl)[1,2,4] triazolo[4,3-b]pyridazin-3(2H)-one 0.552 g of 6-[3-[4-(diphenylmethoxy)piperidino] propoxy][1,2,4]triazolo[4,3-b]pyridazin-3(2H)-one was suspended in 3 ml of N,N-dimethylformamide; 0.200 g of potassium carbonate and 0.209 ml of chloromethyl pivalate were added, followed by stirring at room temperature for 20 hours. After ice water was added, the reaction mixture was extracted with ethyl acetate; the extract was washed with saline and dried over magnesium sulfate. After concentration under reduced pressure, the residue was subjected to silica gel column chromatography and eluted with ethyl acetate-methanol-triethylamine (185:15:2). The desired fraction was collected and concentrated; the crystal obtained was filtered, washed with siethyl ether-hexane (1:1), and dried, to yield 0.515 g of the title compound.

Melting point: 108–110° C.; Elemental analysis (for $C_{32}H_{29}N_5O_5$): Calculated (%): C, 67.00; H, 6.85; N, 12.21; Found (%): C, 66.54; H, 6.76; N, 12.07.

PREPARATION EXAMPLE 1b (1) Compound of Example 9b 10.0 mg
(2) Lactose 60.0 mg
(3) Corn starch 35.0 mg
(4) Gelatin 3.0 mg
(5) Magnesium stearate 2.0 mg A mixture of 10.0 mg of the compound obtained in Example 9b, 60.0 mg of lactose and 35.0 mg of corn starch was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

PREPARATION EXAMPLE 2b (1) Compound of Example 9b 10.0 mg
(2) Lactose 70.0 mg
(3) Corn starch 50.0 mg
(4) Soluble starch 7.0 mg
(5) Magnesium stearate 3.0 mg After 10.0 mg of the compound obtained in Example 9b and 3.0 mg of magnesium stearate were granulated using 0.07 ml of an aqueous solution of soluble starch (containing 7.0 mg of soluble starch), the resulting granules were dried and mixed with 70.0 mg of lactose and 50.0 mg of corn starch. The mixture was compressed to yield tablets.

PREPARATION EXAMPLE 3b (1) Compound of Example 9b 5.0 mg
(2) Sodium chloride 20.0 mg
(3) Distilled water was added to reach a total volume of 2 ml.

5.0 mg of the compound obtained in Example 9b and 20.0 mg of sodium chloride were dissolved in distilled water and diluted with water to reach a total volume of 2.0 ml. The resulting solution was filtered and aseptically packed in a 2 ml ampule. After sterilization, the ampule was sealed to yield a solution for injection.

EXPERIMENTAL EXAMPLE 1b

In the same manner as Experimental Example 1a, the effects of various example compounds on histamine-induced skin reactions in guinea pigs were examined. The results are shown in Table 3.

TABLE 3

Effects of Test Compounds on Histamine-induced Skin Vascular Permeability

| Compound | Suppression (%) of histamine-induced skin vascular permeability elevation, oral administration at 3 mg/kg |
| --- | --- |
| Example 3b | 94 |
| Example 4b | 92 |
| Example 7b | 89 |
| Example 8b | 74 |

EXPERIMENTAL EXAMPLE 2b

In the same manner as Experimental Example 2a, the percent suppression of $LTB_4$-induced chemotactic reactions by various example compounds was calculated. The results are shown in Table 4.

TABLE 4

Effects on $LTB_4$-induced Chemotactic Reaction in Guinea Pig Eosinophils

| Compound | Suppression rate (%) |
| --- | --- |
| Example 7b | 26 |
| Example 8b | 57 |
| Example 10b | 55 |
| Example 11b | 100 |

INDUSTRIAL APPLICABILITY

Compound (I) of the present invention, or a salt thereof, or a pro-drug thereof exhibits excellent anti-allergic activity, anti-histaminic activity, anti-inflammatory activity, anti-PAF (platelet-activating factor) activity, eosinophil chemotaxis-inhibiting activity, and the like, and can be safely used as an anti-allergic agent. Furthermore, Compound (I) of the present invention, or a salt thereof, or a pro-drug thereof exhibits an eosinophil chemotaxis-inhibiting activity as well as an anti-histaminic activity, and can be used to prevent or treat allergic diseases such as chronic urticaria and other forms of urticaria (e.g., acute urticaria), atopic dermatitis, allergic rhinitis, allergic conjunctivitis and hypersensitivity pneumonitis; dermal diseases (especially allergic dermal diseases) such as itching, herpetic dermatitis, eczematous dermatitis, contact dermatitis, prurigo and psoriasis; respiratory diseases such as eosinophilic pneumonia (PIE syndrome), chronic obstructive pulmonary disease (COPD), and asthma; etc.

What is claimed is:

1. A compound represented by the formula:

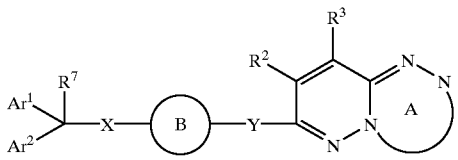

(I)

wherein Ring A is a ring represented by the formula:

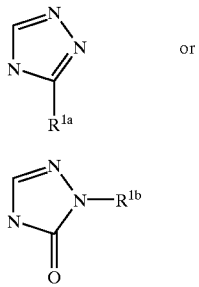

(a)

or (b)

wherein $R^{1a}$ is a hydrogen atom, a halogen atom, an alkyl group optionally having a substituent, an alkenyl group optionally having a substituent, an alkynyl group optionally having a substituent, a cycloalkyl group optionally having a substituent, an aryl group optionally having a substituent, an aralkyl group optionally having a substituent, an acyl group or a hydroxy group having a substituent;

$R^{1b}$ is a hydrogen atom, a halogen atom, an alkyl group optionally having a substituent, an alkenyl group optionally having a substituent, an alkynyl group optionally having a substituent, a cycloalkyl group optionally having a substituent, an aryl group optionally having a substituent, an aralkyl group optionally having a substituent, an acyl group or a hydroxy group optionally having a substituent;

$Ar^1$ and $Ar^2$ are independently a phenyl group optionally having a substituent;

Ring B is a ring represented by the formula:

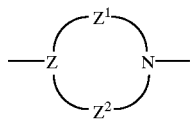

wherein Z is a nitrogen atom or a methine group,
$Z^1$ and $Z^2$ are each independently a linear $C_{1-4}$ alkylene group optionally having a substituent;
X and Y, whether identical or not, are
(i) a bond,
(ii) an oxygen atom,
(iii) S(O)p
wherein p is an integer from 0 to 2,
(iv) $NR^4$
wherein $R^4$ is a hydrogen atom or a lower alkyl group, or
(v) a divalent linear lower hydrocarbon group which may have a substituent, and which may contain 1 to 3 hetero atoms;
$R^2$ and $R^3$, whether identical or not, are a hydrogen atom, a halogen atom, an alkyl group optionally having a substituent, an alkenyl group optionally having a substituent, an alkynyl group optionally having a substituent, a cycloalkyl group optionally having a substituent, an aryl group optionally having a substituent, an aralkyl group optionally having a substituent, an acyl group or a hydroxy group optionally having a substituent;
$R^7$ is a hydrogen atom, a hydroxy group which may be substituted by lower alkyl or a carboxyl group;
or a salt thereof
or a pro-drug thereof.

2. A compound as claimed in claim 1 wherein $Ar^1$ and $Ar^2$ are independently a phenyl group which may be substituted by a halogen atom or $C_{1-6}$ alkyl.

3. A compound as claimed in claim 1 wherein Ring B is a ring represented by the formula:

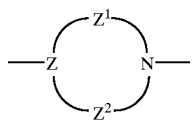

wherein Z is a nitrogen atom or a methine group, $Z^1$ and $Z^2$ are independently a linear $C_{1-4}$ alkylene group which may be substituted by a hydroxy group, an oxo group or a $C_{1-6}$ alkyl group.

4. A compound as claimed in claim 1 wherein X is a bond, an oxygen atom or NH.

5. A compound as claimed in claim 1 wherein Y is
(i) a $C_{1-6}$ alkylene group,
or a group represented by the formula:
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—, (xi) —COO(CH$_2$)p$^1$S—,
(xii) —(CH$_2$)q$^1$O(CH$_2$)q$^2$O—,
(xiii) —(CH$_2$)q$^1$O(CH$_2$)q$^2$NH— or
(xiv) —(CH$_2$)q$^1$O(CH$_2$)q$^2$S— wherein p$^1$ is an integer from 1 to 6, q$^1$ and q are independently an integer from 1 to 3.

6. A compound as claimed in claim 1 wherein Y is a group represented by the formula:

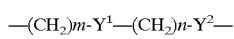

wherein Y$^1$ and Y$^2$ are independently a bond, an oxygen atom, S(O)p (p is an integer from 0 to 2), NR$^4$ (R$^4$ is a hydrogen atom or a lower alkyl group), a carbonyl group, a carbonyloxy group or a group represented by the formula:

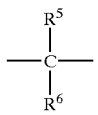

wherein R$^5$ and R$^6$, whether identical or not, are a hydroxy group or a C$_{1-4}$ alkyl group; m and n are independently an integer from 0 to 4 (sum of m and n is not more than 6).

7. A compound as claimed in claim 1 wherein R$^{1a}$ is
(1) a hydrogen atom,
(2) a carboxyl group,
(3) a C$_{1-6}$ alkoxy-carbonyl group,
(4) a C$_{1-6}$ alkyl group which may be substituted by a group selected from the group consisting of (i) cyano, (ii) carboxyl, (iii) C$_{1-6}$ alkoxy-carbonyl and (iv) carbamoyl, or
(5) a carbamoyl group which may be substituted by a C$_{1-6}$ alkyl group optionally having carboxyl or C$_{1-6}$ alkoxy-carbonyl.

8. A compound represented by the formula:

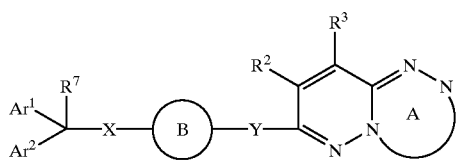

(I)

wherein Ring A is a ring represented by the formula:

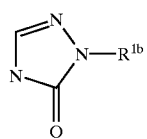

(b)

wherein R$^{1b}$ is (1) a hydrogen atom, or
(2) a C$_{1-6}$ alkyl group which may be substituted by a group selected from the group consisting of
(i) carboxyl,
(ii) C$_{1-6}$ alkoxy-carbonyl,
(iii) C$_{1-6}$ alkyl-carbonyloxy and
(iv) C$_{1-6}$ alkyl-carbonyloxy-C$_{1-6}$ alkoxy-carbonyl;

Ar$^1$ and Ar$^2$ are independently a phenyl group optionally having a substituent;

Ring B is a ring represented by the formula:

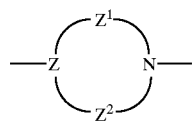

wherein Z is a nitrogen atom or a methine group,
Z$^1$ and Z$^2$ are each independently a linear C$_{1-4}$ alkylene group optionally having a substituent;

X and Y, whether identical or not, are
(i) a bond,
(ii) an oxygen atom,
(iii) S(O)p
   wherein p is an integer from 0 to 2,
(iv) NR$^4$
   wherein R$^4$ is a hydrogen atom or a lower alkyl group, or
(v) a divalent linear lower hydrocarbon group which may have a substituent, and which may contain 1 to 3 hetero atoms;

R$^2$ and R$^3$, whether identical or not, are a hydrogen atom, a halogen atom, an alkyl group optionally having a substituent, an alkenyl group optionally having a substituent, an alkynyl group optionally having a substituent, a cycloalkyl group optionally having a substituent, an aryl group optionally having a substituent, an aralkyl group optionally having a substituent, an acyl group or a hydroxy group optionally having a substituent;

R$^7$ is a hydrogen atom, a hydroxy group which may be substituted by lower alkyl or a carboxyl group;
or a salt thereof
or a pro-drug thereof.

9. A compound as claimed in claim 1 wherein R$^2$ and R$^3$ are a hydrogen atom.

10. A compound as claimed in claim 1 wherein R$^7$ is a hydrogen atom or a hydroxy group.

11. A compound as claimed in claim 1 wherein Ar$^1$ and Ar$^2$ are independently a phenyl group which may be substituted; Ring B is a ring represented by the formula:

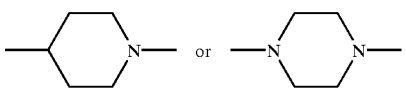

X is a bond or an oxygen atom;
Y is a group represented by the formula:

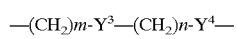

wherein Y$^3$ is a bond or —CH(OH)—, Y$^4$ is an oxygen atom, S or NH, and m and n are independently an integer from 0 to 6 (sum of m and n is not more than 6);

R$^{1a}$ is
(1) a hydrogen atom,
(2) a carboxyl group,
(3) a C$_{1-6}$ alkoxy-carbonyl group,
(4) a C$_{1-6}$ alkyl group which may be substituted by a group selected from the group consisting of (i) cyano, (ii) carboxyl, (iii) C$_{1-6}$ alkoxy-carbonyl and (iv) carbamoyl, or
(5) a carbamoyl group which may be substituted by a C$_{1-6}$ alkyl group optionally having carboxyl or C$_{1-6}$ alkoxy-carbonyl;

$R^{1b}$ is
 (1) a hydrogen atom, or
 (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl;

$R^2$, $R^3$ and $R^7$ are a hydrogen atom.

12. A compound represented by the formula:

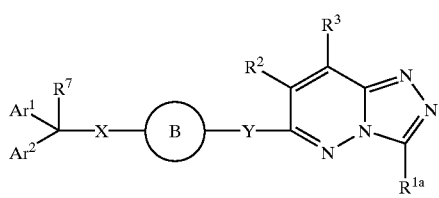
(Ia)

wherein the symbols have the same definitions as those shown in claim 1, or a salt thereof.

13. A compound as claimed in claim 12 wherein $Ar^1$ and $Ar^2$ are independently a phenyl group which may be substituted: Ring B is a ring represented by the formula:

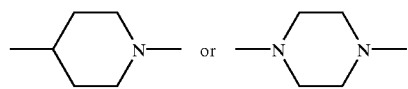

X is a bond or an oxygen atom; Y is a group represented by the formula:

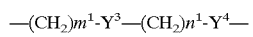

—(CH$_2$)$m^1$-Y$^3$—(CH$_2$)$n^1$-Y$^4$— wherein $Y^3$ is a bond or —CH(OH)—, $Y^4$ is an oxygen atom, S or NH, and $m^1$ and $n^1$ are independently an integer from 0 to 4 (sum of $m^1$ and $n^1$ is not more than 6); $R^{1a}$ is (1) a hydrogen atom, (2) a carboxyl group, (3) a $C_{1-6}$ alkoxy-carbonyl group, (4) a $C_{1-6}$ alkyl group which may be substituted by a group selected from the group consisting of (i) cyano, (ii) carboxyl, (iii) $C_{1-6}$ alkoxy-carbonyl and (iv) carbamoyl, or (5) a carbamoyl group which may be substituted by a $C_{1-6}$ alkyl group optionally having carboxyl or $C_{1-6}$ alkoxy-carbonyl; and $R^2$, $R^3$ and $R^7$ are a hydrogen atom.

14. ① 6-[6-[4-(diphenylmethoxy)piperidino]hexyloxy][1,2,4]triazolo[4,3-b]pyridazine,
 ② 6-[6-[4-(diphenylmethoxy)piperidino]hexylamino][1,2,4]triazolo[4,3-b]pyridazine,
 ③ 3-tert-butyl-6-[3-[4-(diphenylmethoxy)piperidino]propoxy][1,2,4]triazolo[4,3-b]pyridazine,
 ④ 6-[3-[4-(diphenylmethoxy)piperidino]propylamino][1,2,4]triazolo[4,3-b]pyridazine-3-carboxylic acid, or a salt thereof.

15. A compound represented by the formula:

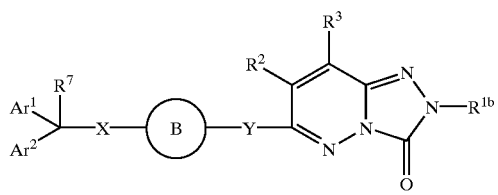
(Ib)

wherein the symbols have the same definitions as those shown in claim 1, or a salt thereof.

16. A compound as claimed in claim 15 wherein the partial structural formula:

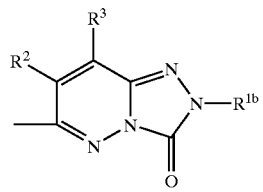

represents the formula:

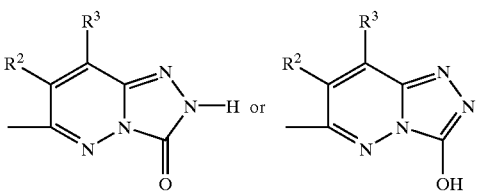

provided that $R^{1b}$ is a hydrogen atom.

17. A compound as claimed in claim 15 wherein $Ar^1$ and $Ar^2$ are independently a phenyl group which may be substituted; Ring B is a ring represented by the formula:

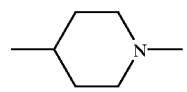

X is an oxygen atom; Y is a group represented by the formula:

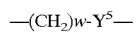

—(CH$_2$)$w$-Y$^5$— wherein w is an integer from 1 to 6, and $Y^5$ is an oxygen atom or NH; $R^{1b}$ is
 (1) a hydrogen atom, or
 (2) a $C_{1-6}$ alkyl group which may be substituted by a group selected from the group consisting of (i) carboxyl, (ii) $C_{1-6}$ alkoxy-carbonyl, (iii) $C_{1-6}$ alkyl-carbonyloxy and (iv) $C_{1-6}$ alkyl-carbonyloxy-$C_{1-6}$ alkoxy-carbonyl; and $R^2$, $R^3$ and $R^7$ are a hydrogen atom.

18. ① 6-[3-[4-(diphenylmethoxy)piperidino]propylamino][1,2,4]triazolo[4,3-b]pyridazin-3(2H)-one,
 ② ethyl 2-[6-[3-[4-(diphenylmethoxy)piperidino]propylamino]-3-oxo[1,2,4]triazolo[4,3-b]pyridazin-2(3H)-yl]-2-methylpropionate,
 ③ 2-[6-[3-[4-(diphenylmethoxy)piperidino]propylamino]-3-oxo[1,2,4]triazolo[4,3-b]pyridazin-2(3H)-yl]-2-methylpropionic acid, ④ pivaloyloxymethyl 2-[6-[3-[4-(diphenylmethoxy)piperidino]propylamino]-3-oxo[1,2,4]triazolo[4,3-b]pyridazin-2(3H)-yl]-2-methylpropionate,
⑤ pivaloyloxymethyl 2-[6-[3-[4-(diphenylmethoxy)piperidino]propoxy]-3-oxo[1,2,4]triazolo[4,3-b]pyridazin-2(3H)-yl]-2-methylpropionate, or a salt thereof.

19. A method for producing a compound as claimed in claim 1, which comprises reacting a compound represented by the formula:

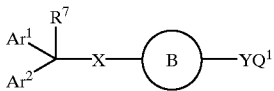

wherein $Q^1$ represents a leaving group; the other symbols have the same meanings as defined in claim 1, or a salt thereof, with a compound represented by the formula:

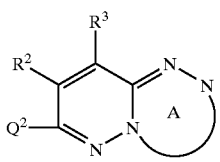

wherein $Q^2$ represents a leaving group; the other symbols have the same meanings as defined in claim 1, or a salt thereof.

20. A method for producing a compound as claimed in claim 12, which comprises reacting a compound represented by the formula:

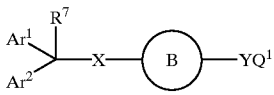

wherein $Q^1$ represents a leaving group; the other symbols have the same meanings as defined in claim 1, or a salt thereof, with a compound represented by the formula:

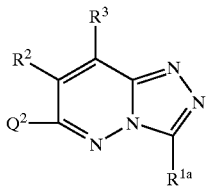

wherein $Q^2$ represents a leaving group; the other symbols have the same meanings as defined in claim 1, or a salt thereof.

21. A method for producing a compound as claimed in claim 15, which comprises reacting a compound represented by the formula:

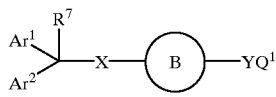

wherein $Q^1$ represents a leaving group; the other symbols have the same meanings as defined in claim 15, or a salt thereof, with a compound represented by the formula:

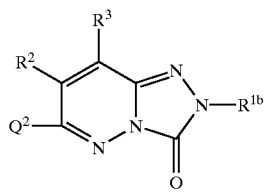

wherein $Q^2$ represents a leaving group; the other symbols have the same meanings as defined in claim 15, or a salt thereof.

22. A pharmaceutical composition comprising:

a compound as claimed in claim 1; and a pharmaceutically acceptable excipient, binder, disintegrating agent, additive, solvent or carrier.

23. A pharmaceutical composition as claimed in claim 22 which is an anti-histaminic and/or eosinophil chemotaxis-inhibiting agent.

24. A pharmaceutical composition as claimed in claim 22 which is an anti-allergic agent.

25. A pharmaceutical composition as claimed in claim 22 which is an agent for preventing or treating asthma, allergic conjunctivitis, allergic rhinitis, chronic urticaria or atopic dermatitis.

26. A method for suppressing histamine, eosinophil chemotaxis or a combination thereof comprising administering an effective amount of a compound as claimed in claim 1 to mammals.

27. A method for treating allergic diseases comprising administering an effective amount of a compound as claimed in claim 1 to mammals.

28. A method for treating asthma, allergic conjunctivitis, allergic rhinitis, chronic urticaria or atopic dermatitis which comprises administering an effective amount of a compound as claimed in claim 1 to mammals.

* * * * *

UNITED STATES PATENT AND TRADEMARK OFFICE
CERTIFICATE OF CORRECTION

PATENT NO.   : 6,610,694 B1
DATED        : August 26, 2003
INVENTOR(S)  : Yasuhiko Kawano, Hideaki Nagaya and Michiyo Gyoten It is certified that error appears in the above-identified patent and that said Letters Patent is hereby corrected as shown below:

<u>Column 4,</u>
Line 17, replace "triazolone" with -- triazolo --

Signed and Sealed this

Ninth Day of December, 2003

JAMES E. ROGAN
*Director of the United States Patent and Trademark Office*